(12) United States Patent
Im et al.

(10) Patent No.: US 12,161,662 B2
(45) Date of Patent: Dec. 10, 2024

(54) STRUCTURAL AND FUNCTIONAL CHARACTERISTICS OF YEAST-DERIVED POLYSACCHARIDE INDUCING TREG CELL

(71) Applicants: INSTITUTE FOR BASIC SCIENCE, Daejeon (KR); POSTECH ACADEMY-INDUSTRY FOUNDATION, Pohang-si (KR)

(72) Inventors: Sin-Hyeog Im, Pohang-si (KR); Verma Ravi, Pohang-si (KR); Changhon Lee, Pohang-si (KR)

(73) Assignees: INSTITUTE FOR BASIC SCIENCE, Daejeon (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 827 days.

(21) Appl. No.: 17/285,253

(22) PCT Filed: Jul. 29, 2019

(86) PCT No.: PCT/KR2019/009422
§ 371 (c)(1),
(2) Date: Apr. 14, 2021

(87) PCT Pub. No.: WO2020/080653
PCT Pub. Date: Apr. 23, 2020

(65) Prior Publication Data
US 2021/0369766 A1  Dec. 2, 2021

(30) Foreign Application Priority Data
Oct. 17, 2018 (KR) .................. 10-2018-0123814

(51) Int. Cl.
*A61K 31/736* (2006.01)
*A23L 33/125* (2016.01)
(Continued)

(52) U.S. Cl.
CPC .......... *A61K 31/736* (2013.01); *A23L 33/125* (2016.08); *A23L 33/145* (2016.08);
(Continued)

(58) Field of Classification Search
CPC ...... A61K 31/716; A61K 31/715; A61P 37/02
See application file for complete search history.

(56) References Cited

U.S. PATENT DOCUMENTS

2011/0250235 A1  10/2011  Saarinen et al.

FOREIGN PATENT DOCUMENTS

| CN | 102257011 | 11/2011 |
| CN | 107050427 | 8/2017 |

(Continued)

OTHER PUBLICATIONS

Riley et al., "Human T Regulatory Cell Therapy: Take a Billion or So and Call Me in the Morning" Immunity Review vol. 30 pp. 656-665 DOI 10.1016/j.immuni.2009.04.006 (Year: 2009).*

(Continued)

*Primary Examiner* — Eric Olson
(74) *Attorney, Agent, or Firm* — LEX IP MEISTER, PLLC

(57) ABSTRACT

The present invention relates to a yeast-derived polysaccharide inducing Treg cells and a use thereof and, more particularly, to a polysaccharide comprising mannan and β-glucan, an composition for immunomodulation comprising the polysaccharide as an active ingredient, a pharmaceutical composition or food comprising the polysaccharide as an active ingredient for prevention or treatment of immune disease or inflammatory disease, a method for preparation of regulatory T cells by using the polysaccharide, a cell therapeutic agent comprising the regulatory T cells prepared by the preparation method as an active ingredient, and a treatment method using same. Even at a low dose, the novel (Continued)

polysaccharide according to the present invention allows the production of tolerogenic antigen presenting cells through the β-glucan and mannan structure retained therein, whereby the novel polysaccharide can induce the differentiation or production of antigen-specific regulatory T cells (Treg cells) to modulate the target immune system with low adverse effects. Therefore, MGCP and the Treg cells induced by the polysaccharide are effective for preventing or treating immune disease or inflammatory disease.

12 Claims, 12 Drawing Sheets

Specification includes a Sequence Listing.

(51) Int. Cl.
| | |
|---|---|
| A23L 33/145 | (2016.01) |
| A61K 31/715 | (2006.01) |
| A61K 31/716 | (2006.01) |
| A61K 36/06 | (2006.01) |
| A61K 39/00 | (2006.01) |
| A61P 1/00 | (2006.01) |
| A61P 29/00 | (2006.01) |
| A61P 37/02 | (2006.01) |
| C08B 37/00 | (2006.01) |
| C12N 5/0783 | (2010.01) |

(52) U.S. Cl.
CPC .......... *A61K 31/715* (2013.01); *A61K 31/716* (2013.01); *A61K 36/06* (2013.01); *A61K 39/4611* (2023.05); *A61K 39/4621* (2023.05); *A61K 39/46433* (2023.05); *A61P 1/00* (2018.01); *A61P 29/00* (2018.01); *A61P 37/02* (2018.01); *C08B 37/0087* (2013.01); *C12N 5/0637* (2013.01); *A23V 2002/00* (2013.01); *C12N 2501/90* (2013.01); *C12N 2502/1121* (2013.01)

(56) References Cited

FOREIGN PATENT DOCUMENTS

| JP | 04-58893 | 2/1992 |
|---|---|---|
| JP | 2003-012701 | 1/2003 |
| JP | 2008-541700 | 11/2008 |
| KR | 10-1999-0028736 | 4/1999 |
| WO | 2010070207 | 6/2010 |
| WO | 2016117960 | 7/2016 |
| WO | 2018/139660 | 8/2018 |

OTHER PUBLICATIONS

Mikami et al., "Mitogenic Effect of the Mannans from *Saccharomyces cerevisiae* on Mouse Spleen Lymphocytes" Microbiol. Immuol. vol. 26 No. 10 pp. 913-922 (Year: 1982).*
Aimanianda et al., "Cell Wall beta-(1,6)-Glucan of *Saccharomyces cerevisiae*: Structural Characterization and in Situ Synthesis" The Journal of Biological Chemistry vol. 284 No. 20 pp. 13401-13412 (Year: 2009).*
Kocourek et al., "Method for Fingerprinting Yeast Cell Wall Mannans" Journal of Bacteriology vol. 100 No. 3 pp. 1175-1181 (Year: 1969).*
Nandi et al., "Antioxidant and immunostimulant beta-glucan from edible mushroom *Russula albonigra* (Krombh.) Fr." Carbohydrate Polymers vol. 99 pp. 774-782, DOI: 10.1016/j.carbpol.2013.09.016 (Year: 2014).*
Iorio et al., "Candida albicans cell wall comprises a branched b-D-(1,6)-glucan with b-D-(1,3)-side chains" Carbohydrate Research vol. 343 pp. 1050-1061, doi: 10.1016/j.carres.2008.02.020 (Year: 2008).*

Samanta et al., "Structural characterization of an immunoenhancing glucan isolated from a mushroom *Macrolepiota dolichaula*" International Journal of Biological Macromolecules vol. 61 pp. 89-96, DOI: 10.1016/j.ijbiomac.2013.06.010 (Year: 2013).*
Fahlquist-Hagert et al., "Variants of beta-glucan polysaccharides downregulate autoimmune inflammation" Communications Biology vol. 5 p. 449, DOI: 10.1038/s42003-022-03376-y (Year: 2022).*
Song Wengang, "Medical Immunology" Jiangsu Phoenix Science and Technology Press, p. 140, Jul. 2018, Exerpt only.
SIPO, Final Office Action of the CN patent application No. 201980076486.8 dated Sep. 30, 2022.
Mao Zhonggui, "2. Yeast cell wall", Downstream Technology in Bioindustry, China Light Industry Press, Oct. 1999.
Mei Zhang et al., "Optimizing Tumor Microenvironment for Cancer Immunotherapy: β-Glucan-Based Nanoparticles", Front. Immunol., vol. 9, Article 341, Feb. 26, 2018.
SIPO, Office Action of CN 201980076486.8 dated Dec. 20, 2021.
SIPO, Search Report of CN 201980076486.8 dated Dec. 10, 2021.
Stier, Heike, et al. "Immune-modulatory effects of dietary Yeast Beta-1, 3/1, 6-D-glucan." Nutrition journal 13.1 (Apr. 28, 2014): 1-9.
Camilli, Giorgio, et al. "The complexity of fungal β-glucan in health and disease: effects on the mononuclear phagocyte system." Frontiers in immunology 9 (Apr. 16, 2018): 673.
Lee, Changhon, et al. "Structural specificities of cell surface β-glucan polysaccharides determine commensal yeast mediated immunomodulatory activities." Nature communications 12.1 (Jun. 14, 2021): 1-16.
JPO, Office Action of the corresponding Japanese Patent Application No. 2021-521531 dated Jun. 27, 2022.
EPO, Supplementary European Search Report of the corresponding EP patent application No. 19874049.0 dated Jun. 22, 2022.
KIPO, Office Action of KR 10-2019-0091908 dated Aug. 24, 2020.
Alizadeh, M., "Yeast products as potential sources of immunomodulatory and growth promoting activity for broiler chickens", 2015, Ph.D. thesis., Department of Animal Science, University of Manitoba.
Eurofins Homepage., "Yeast cell wall polysaccharides: β-glucans & mannans", Jan. 4, 2018, pp. 1-2, URL:https://cdnmedia.eurofins.com/corporate-eurofins/media/12145195/yeast_cell_wall_polysaccharides.pdf.
Im, S.-H., "Reprogramming of the immune system by rationally selected probiotics", In: The 13th Regular Seminar on 2018 1st Semester of Department of Biotechnology., Jun. 7, 2018, Unist, Bldg 110 Room N104, URL:http://SLS.unist.ac.kr/ko/_newsevent/seminar_view.asp?seq=1320 (abstract only).
Lee, C. et al., "Structure and functional characterization of yeast derived polysaccharides in inducing Treg cells", p. 104, In: Kai International Meeting 2018, Nov. 7-9, 2018, Sejong University Convention Center, Seoul, Korea.
Nadine Cerf-Bensussan et al., "The immune system and the gut microbiota: friends or foes?", Nat. Rev. Immunol. 2010;10(10):735-44.
Matthew L. Wheeler et al., "Immunity to Commensal Fungi: Detente and Disease", Annu Rev Pathol. Jan. 24, 2017; 12: 359-385. doi:10.1146/annurev-pathol-052016-100342.
Iliyan D. Iliev et al., "Fungal dysbiosis: immunity and interactions at mucosal barriers", Nat Rev Immunol. Oct. 2017 ; 17(10): 635-646. doi:10.1038/nri.2017.55.
David M. Underhill et al., "The mycobiota: interactions between commensal fungi and the host immune system", Nat Rev Immunol. Jun. 2014 ; 14(6): 405-416. doi:10.1038/nri3684.
Sky W. Brubaker et al., "Innate Immune Pattern Recognition: A Cell Biological Perspective", AAnnu Rev Immunol. 2015 ; 33: 257-290. doi:10.1146/annurev-immunol-032414-112240.
Yukihiro Furusawa et al., "Commensal microbe-derived butyrate induces the differentiation of colonic regulatory T cells", Nature 504:446-450, 2013. doi:10.1038/nature12721.
Sarkis K. Mazmanian et al., "An Immunomodulatory Molecule of Symbiotic Bacteria Directs Maturation of the Host Immune System", Cell, vol. 122, 107-118, Jul. 15, 2005. DOI 10.1016/j.cell.2005.05.007.

(56) References Cited

OTHER PUBLICATIONS

Ochoa-Reparaz et al., "Central Nervous System Demyelinating Disease Protection by the Human Commensal Bacteroides fragilis Depends on Polysaccharide A Expression", The Journal of Immunology 185:4101-4108, 2010.
Ravi Verma et al., "Cell surface polysaccharides of Bifidobacterium bifidum induce the generation of Foxp3+ regulatory T cells", Science immunology 3 (28), eaat6975, Oct. 19, 2018.
Arthur O. Tzianabos et al., "Polysaccharide Immunomodulators as Therapeutic Agents: Structural Aspects and Biologic Function", Clinical Microbiology Reviews, vol. 13, No. 4, Oct. 2000, p. 523-533.
Giorgio Camilli et al., "The Complexity of Fungal β-Glucan in Health and Disease: effects on the Mononuclear Phagocyte System", Frontiers in Immunology, vol. 9, Article 673, Apr. 16, 2018.
Viviam de Oliveira Silva et al., "Promising Effects of Beta-Glucans on Metabolism and on the Immune Responses: Review Article", American Journal of Immunology 2017, 13 (1): 62.72.
Beini Sun et al., "Polysaccharides as vaccine adjuvants", Vaccine 2018;36(35):5226-34.
M. Novak et al., "β-Glucans, History, and the Present: Immunomodulatory Aspects and Mechanisms of Action", Journal of Immunotoxicology, 5:47-57, 2008. DOI: 10.1080/15476910802019045.
Nicole Dalonso et al., "β-(1→3),(1→6)-Glucans: medicinal activities, characterization, biosynthesis and new horizons", Appl Microbiol Biotechnol 99, 7893-7906 (2015). https://doi.org/10.1007/s00253-015-6849-x.
Kwang-Ho Lee et al., "Bacterial β-(1,3)-glucan prevents DSS-induced IBD by restoring thereduced population of regulatory T cells", Immunobiology 219 (2014) 802-812.
Shinobu Saijo et al., "Dectin-2 Recognition of a-Mannans and Induction of Th17 Cell Differentiation Is Essential for Host Defense against Candida albicans", Immunity 32, 681-691, May 28, 2010.
Benjamin N. Gantner et al., "Collaborative Induction of Inflammatory Responses by Dectin-1 and Toll-like Receptor 2", J. Exp. Med. 2003; 197(9):1107-17.
Subha Karumuthil-Melethil et al., "TLR2- and Dectin 1-Associated Innate Immune Response Modulates T-Cell Response to Pancreatic b-Cell Antigen and Prevents Type 1 Diabetes", Diabetes 2015; 64(4):1341-57.
Stephanie Dillon et al., "Yeast zymosan, a stimulus for TLR2 and dectin-1, induces regulatory antigenpresenting cells and immunological tolerance", J. Clin. Invest. 2006;116(4):916-28, Apr. 2006.
Fiona Powrie et al., "Inhibition of Th1 Responses Prevents Inflammatory Bowel Disease in scid Mice Reconstituted with CD45RBhi CD4+ T Cells", Immunity 1994;1(7):553-62.
Michael W. Leach et al., "Inflammatory Bowel Disease in C.B-17 scid Mice Reconstituted with the CD45RBhigh Subset of CD4+ T Cells", Amenican Journal of Pathology, vol. 148, No. 5, May 1996.
Tze Guan Tan et al., "Identifying species of symbiont bacteria from the human gut that, alone, can induce intestinal Th17 cells in mice", PNAS, Dec. 13, 2016, 113 (50) E8141-E8150; first published Nov. 23, 2016.
Neil A. R. Gow et al., "The Fungal Cell Wall: Structure, Biosynthesis, and Function", Microbiol. Spectr. 2017;5(3), May 19, 2017.
JPO, Office Action of the corresponding Japanese Patent Application No. 2021-521531 dated Jan. 19, 2023.
M V Sanguedolce et al., "Zymosan-stimulated tumor necrosis factor-alpha production by human monocytes", J Immunol Apr. 1, 1992, 148 (7) 2229-2236.

\* cited by examiner

|      | Man | Gal | Glc |
|------|-----|-----|-----|
| MGCP | 5.4 | 0.3 | 1   |

MGCP fraction A

MGCP fraction B

MGCP fraction C

STRUCTURAL AND FUNCTIONAL CHARACTERISTICS OF YEAST-DERIVED POLYSACCHARIDE INDUCING TREG CELL

TECHNICAL FIELD

The present invention relates to a yeast-derived polysaccharide inducing Treg cells and the use thereof and, more particularly, to a polysaccharide containing mannan and β-glucan, an composition for immunomodulation comprising the polysaccharide as an active ingredient, a pharmaceutical composition or food containing the polysaccharide as an active ingredient for preventing or treating an immune disease or inflammatory disease, a method for preparing regulatory T cells using the polysaccharide, a cell therapeutic agent containing the regulatory T cells prepared by the method as an active ingredient, and a method of treating an immune disease or inflammatory disease comprising administering the cell therapeutic agent to a subject.

BACKGROUND ART

Mammals contain a biota of microorganisms that continually interact with the immune system. Symbiotic microorganisms form symbiotic relationships with the host and interact with the host in various processes such as digestion, behaviors and maturation of the immune system (Cerf-Bensussan N., Gaboriau-Routhiau V. The immune system and the gut microbiota: friends or foes? Nat. Rev. Immunol. 2010;10(10):735-44.). Similarly, fungi are present in the human body and affect the immune system of the host (Wheeler M. L., Limon J. J., Underhill D. M. Immunity to Commensal Fungi: Detente and Disease. Annu. Rev. Pathol. 2017;12:359-85.). Innate immune cells detect a variety of pathogen-associated molecular patterns (PAMPs) on the surface of fungal cells, comprising polysaccharides, through pattern recognition receptors (PRRs) such as Toll-like receptors (TLRs). Upon detection of a signal, innate immune cells change the gene expression profile and produce immune signaling molecules such as cytokines in order to regulate acquired immunity (Iliev I. D., Leonardi I. Nat. Rev. Immunol. 2017;17(10):635-46., Underhill D. M., Iliev I. D. Nat. Rev. Immunol. 2014;14(6):405-16. and Brubaker S. W., Bonham K. S., Zanoni I., et al. Annu. Rev. Immunol. 2015;33:257-90.).

These symbiotic microorganisms regulate the development and differentiation of certain lineages of CD4 cells, such as T helper 17 cells (Th17) or regulatory T cells (Treg cells). Treg cells belong to a subset of CD4+ cells having an immunosuppressive function, and are characterized by the expression of the transcription factor Foxp3. Treg cells are largely divided into thymus-derived cells (nTreg cells) and non-thymus-derived cells, depending on the location of production thereof, and are divided into Treg cells (iTregs or pTregs) derived from CD4+ Tnaive cells in the secondary immune system. Enrichment of Treg cells in vivo can control various hyperimmune diseases such as autoimmune and allergic diseases. The molecular mechanisms underlying the generation of these Treg cells have not been clearly elucidated yet, but several studies have reported that metabolites produced by bacteria or polysaccharides derived from cell walls having specific chemical structures can promote the differentiation of Treg cells. For example, butyrate has been reported as a major effector molecule inducing the differentiation of colon Treg cells in the presence of Clostridia (Furusawa et al., Nature 504:446-450, 2013). Polysaccharide A (PSA), which is a zwitterionic polysaccharide of B. fragilis, has been identified as an effector immunomodulatory agent essential for the induction of IL-10-producing Treg cells (Mazmanian et al., Cell 122:107-118, 2005; Ochoa-Reparaz et al., The Journal of Immunology 185:4101-4108, 2010). It has also been reported that CSGG, etc. which is a cell surface polysaccharide derived from Bifidobacterium bifidum, can induce the differentiation of Treg cells (Ravi Verma et al., Science immunology 3 (28), eaat6975).

In order to use such microorganisms or metabolites thereof in the treatment of diseases of patients, some patients have to regulate an overactive immune response (i.e., in the case of allergic or autoimmune disease), while other patients have to strengthen the immune system (i.e., in the case of cancer or viral infection). For example, when Bifidobacterium, which is a Th17-induced probiotic, was administered to a rheumatoid arthritis animal model, arthritis symptoms were aggravated (Tze Guan Tan, 113(50):E8141-E8150, 2016). Therefore, it is very important therapeutically to identify beneficial microorganisms and to elucidate the mechanisms of agonists thereof.

Meanwhile, yeast-derived polysaccharides have immunomodulatory functions and are used as therapeutic agents for activating or regulating the immune system (Tzianabos A. O. Clin. Microbiol. Rev. 2000;13(4):523-33.) Beta-glucan is the most abundant polysaccharide in fungal cell walls, having complicated and various structures (Camilli G., Tabouret G., Quintin J. The Complexity of Fungal beta-Glucan in Health and Disease: Effects on the Mononuclear Phagocyte System.). They are known to modulate biological responses that affect the immune response (Silva VdO, de Moura N. O., de Oliveira L. J. R., et al. Promising Effects of Beta-Glucans on Metabolism and on the Immune Responses: Review Article.).

In general, researchers have used beta-glucan as a therapeutic agent for infectious diseases or a therapeutic adjuvant for cancer (Sun B., Yu S., Zhao D., et al. Vaccine 2018;36 (35):5226-34. and Novak M., Vetvicka V. J. Immunotoxicol. 2008;5(1):47-57.). Meanwhile, some studies have reported that beta-glucan has anti-inflammatory functions (Dalonso N., Goldman G. H., Gern R. M. Appl. Microbiol. Biotechnol. 2015;99(19):7893-906. and Lee K. H., Park M., Ji K. Y., et al. Bacterial beta-(1,3)-glucan prevents DSS-induced IBD by restoring the reduced population of regulatory T cells.). Similar to fungal beta-glucan, fungal mannan has also been reported to play an immunomodulatory role (Saijo S., Ikeda S., Yamabe K., et al. Dectin-2 recognition of alpha-mannans and induction of Th17 cell differentiation is essential for host defense against Candida albicans.). However, although the role of polysaccharides as an immune modulator has been reported, the exact elements and mechanisms by which polysaccharides regulate the immune system have not been clearly elucidated. In particular, the immune responses (immunity enhancement or hyperimmune regulation responses) that occur in different manners depending on the structure and molecular weight of the polysaccharide have not been precisely defined. It is very important to elucidate the same in order to redesign (alter) an undesired immune response observed in connection with a specific disease in a desired pattern for application to the development of therapeutic agents for diseases.

Zymosan is a yeast ghost cell (Saccharomyces cerevisiae), and most yeasts have similar cell wall components. The yeast cell wall has a two-layered structure divided into an outer membrane composed of mannan and an inner membrane composed of glucans having a complicated structure comprising a plurality of layers of β-1,3-linked glucans connected through β1,6-glucan (Gow NAR, Latge J. P., Munro C. A. The Fungal Cell Wall: Structure, Biosynthesis, and Function. Microbiol. Spectr. 2017;5(3)). The polysaccharides of zymosan are mainly composed of β-glucans and mannans, which are structurally similar to those of yeast. In many other studies, zymosan has been used to study the role of fungal polysaccharides on the immune system, but the results of these studies are controversial. Some studies have shown that zymosan exacerbates inflammatory diseases by activating the immune system (Sanguedolce M. V., Capo C., Bongrand P., et al. Zymosan-stimulated tumor necrosis factor-alpha production by human monocytes and Gantner B. N., Simmons R. M., Canavera S. J., et al. J. Exp. Med. 2003;197(9):1107-17), and other studies demonstrated that zymosan may immunologically induce resistance by inducing IL-10-producing immune-tolerant antigen-presenting cells that inhibit antigen-specific T cell responses in order to alleviate autoimmune diseases (Karumuthil-Melethil S., et al. Diabetes 2015; 64(4):1341-57. and Dillon S., Agrawal S., Banerjee K., et al. J. Clin. Invest. 2006;116(4):916-28.).

Under the above technical background, as the result of extensive efforts to accurately identify the elements having an immunomodulatory function in yeast-derived polysaccharides and mechanisms thereof and find substances capable of efficiently inducing the differentiation or production of Treg even at a low dose based thereon, the present inventors purified novel polysaccharides from the yeast cell wall and named the same "MGCP (mannan/beta-glucan-containing polysaccharides)". In addition, the present inventors found that Treg cells can be induced by the MGCP in vitro and in vivo, and β-1,6-glucan is essential for induction of Treg cells by MGCP, and that administration of MGCP or Treg cells induced by MGCP can suppress colitis. Based on these findings, the present invention was completed.

The information disclosed in this Background section is provided only for better understanding of the background of the present invention, and therefore it may not comprise information that forms the prior art that is already obvious to those skilled in the art.

DISCLOSURE

Technical Problem

Therefore, the present invention has been made in view of the above problems, and it is one object of the present invention to provide a novel polysaccharide comprising mannan and beta-glucan β-glucan).

It is another object of the present invention to provide a composition for immunomodulation comprising the polysaccharide as an active ingredient.

It is another object of the present invention to provide a pharmaceutical composition for preventing and treating an immune disease or inflammatory disease comprising the polysaccharide as an active ingredient.

It is another object of the present invention to provide a food for preventing or ameliorating an immune disease or inflammatory disease comprising the polysaccharide as an active ingredient.

It is another object of the present invention to provide a method of preventing or treating an immune disease or inflammatory disease comprising administering a composition comprising the polysaccharide as an active ingredient to a subject.

It is another object of the present invention to provide the use of a composition comprising the polysaccharide as an active ingredient for the prevention or treatment of an immune disease or inflammatory disease.

It is another object of the present invention to provide a method of producing regulatory T cells (Treg cells) using the polysaccharide.

It is another object of the present invention to provide a cell therapeutic agent for preventing, treating or ameliorating an immune disease or inflammatory disease comprising the regulatory T cells (Treg cells) produced by the method as an active ingredient.

It is another object of the present invention to provide a method for preventing or treating an immune disease or an inflammatory disease comprising administering the cell therapeutic agent to a subject.

It is another object of the present invention to provide the use of the cell therapeutic agent for the prevention or treatment of an immune disease or an inflammatory disease.

Technical Solution

To achieve the above objects, in accordance with one aspect, the present invention provides a polysaccharide comprising mannan and beta-glucan (β-glucan).

In accordance with another aspect, the present invention provides a composition for immunomodulation comprising the polysaccharide as an active ingredient.

In accordance with another aspect, the present invention also provides a pharmaceutical composition for preventing and treating an immune disease or inflammatory disease comprising the polysaccharide as an active ingredient.

In accordance with another aspect, the present invention also provides a food for preventing or ameliorating an immune disease or inflammatory disease comprising the polysaccharide as an active ingredient.

In accordance with another aspect, the present invention also provides a method of preventing or treating an immune disease or inflammatory disease comprising administering the composition comprising the polysaccharide as an active ingredient to a subject.

In accordance with another aspect, the present invention also provides the use of the composition comprising the polysaccharide as an active ingredient for the prevention or treatment of an immune disease or inflammatory disease.

In accordance with another aspect, the present invention also provides a method of producing regulatory T cells (Treg cells), the method comprising treating antigen-presenting cells with the polysaccharide, and then obtaining tolerogenic antigen-presenting cells; and co-incubating the tolerogenic antigen-presenting cells with CD4+ T cells, and then inducing regulatory T cells (Treg cells).

In accordance with another aspect, the present invention also provides a cell therapeutic agent for preventing, treating or ameliorating an immune disease or inflammatory disease comprising the regulatory T cells (Treg cells) produced by the method as an active ingredient.

In accordance with another aspect, the present invention also provides a method for preventing or treating an immune disease or an inflammatory disease comprising administering the cell therapeutic agent to a subject.

In accordance with another aspect, the present invention provides the use of the cell therapeutic agent for the prevention or treatment of an immune disease or an inflammatory disease.

DESCRIPTION OF DRAWINGS

FIG. 1A shows the frequency of CD4+Foxp3+ T cells induced by various concentrations of zymosan.

The indicated amount of zymosan was digested with each cleavage enzyme and then splenic CD11c+ DC was primed with cleaved zymosan before the addition of naive CD4 T cells (FIGS. 1B and 1C).

FIG. 1B shows the frequency of CD4+Foxp3+ T cells induced by β-1,3-glucanase-treated zymosan.

FIG. 1C shows the induction of CD4+Foxp3+ T cells by the indicated enzyme and cleaved zymosan.

Figure 2:
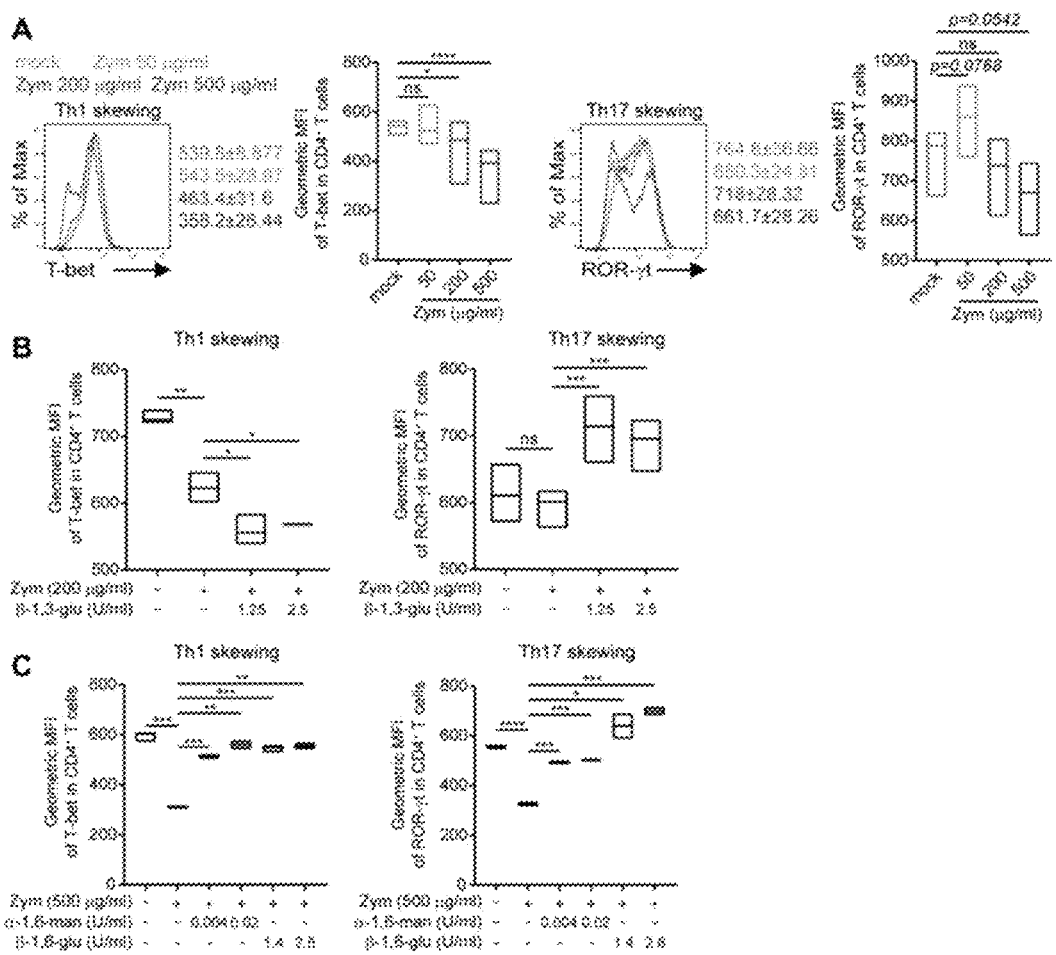

FIG. 2 shows the role of the polysaccharide of the zymosan in the immune response.

Splenic CD11c+ DC was stimulated with different doses of zymosan and then co-incubated with naive CD4 T cells under sub-optimal skewing conditions in the direction of Th1 and Th17 cells, all data in graphs represents mean±SEM, * represents $p<0.05$,  represents $p<0.01$, * represents $p<0.001$, and **** represents $p<0.0001$ (Student's t-test).

FIG. 2A shows flow cytometry plots and MFI of T-bet or RORγt under optimal skewing conditions in the direction of Th1 and Th17 cells.

Certain polysaccharides were removed from the indicated dose of zymosan by treatment with a homologous cleavage enzyme before stimulation of splenic DC. DC co-incubated with naive CD4 T cells in a Th1 or Th17 operating environment was treated with the modified zymosan.

FIG. 2B shows the MFI of T-bet or RORγt by β-1,3-glucan-removed zymosan.

FIG. 2C shows the MFI of T-bet or RORγt by mannosidase- or β-1,6-glucanase-treated zymosan.

Figures 3, 4:
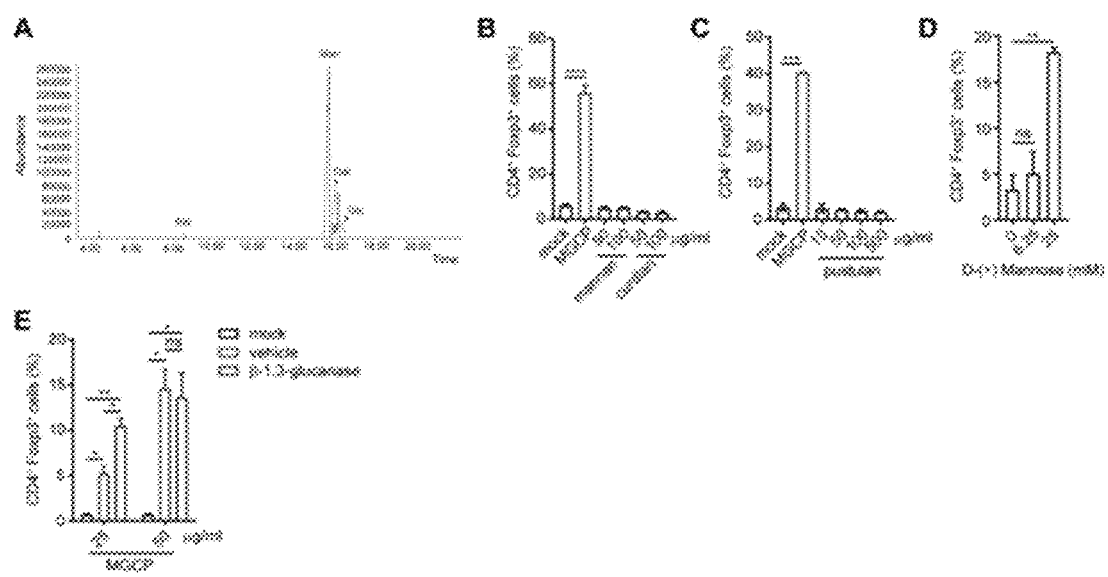

FIG. 3 shows the chemical composition and functional properties of MGCP.

FIG. 3A shows the composition of MGCP.

Splenic DCs were stimulated by indicated polysaccharides before co-incubation with naive CD4 T cells.

FIG. 3B shows the frequency of CD4+Foxp3+ T cells induced by mannan or curdlan (β-1,3-glucan).

FIG. 3C shows the frequency of CD4+Foxp3+ T cells induced by pustulan (linear β-1,6-glucan).

FIG. 3D shows the frequency of CD4+Foxp3+ T cells induced by various concentrations of D-(+) mannose.

FIG. 3E shows the frequency of CD4+Foxp3+ T cells induced by purified MGCP in the intact yeast cell wall or the yeast cell wall from which β-1,3-glucan has been removed.

All data in bar graphs represent mean±SEM, * represents $p<0.05$,  represents $p<0.01$, * represents $p<0.001$, and **** represents $p<0.0001$ (Student's t-test).

FIG. 4 is a table showing the results of analysis of the composition of MGCP.

Figure 5:
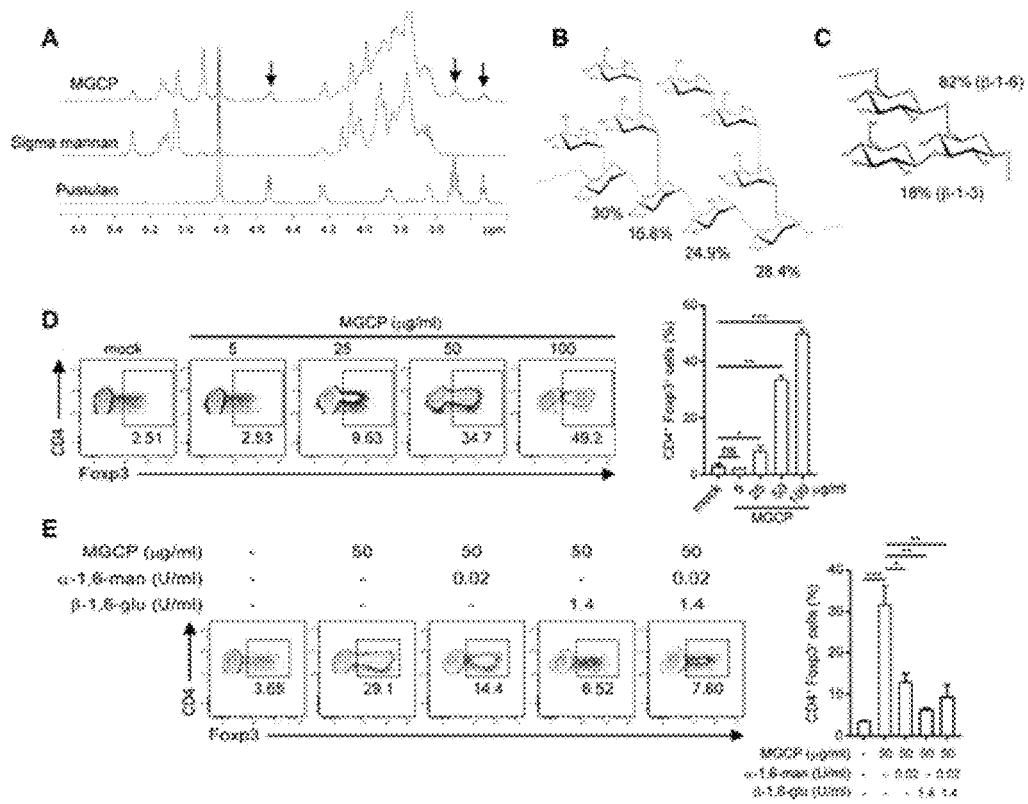

FIG. 5 shows the role of β-1,6-glucan in the differentiation of Treg cells by MGCP.

FIG. 5A shows the proton NMR spectrum of MGCP.

FIG. 5B shows the chemical structure of mannan.

FIG. 5C shows the chemical structure of the β-1,6-glucan moiety of MGCP.

Figure 1:
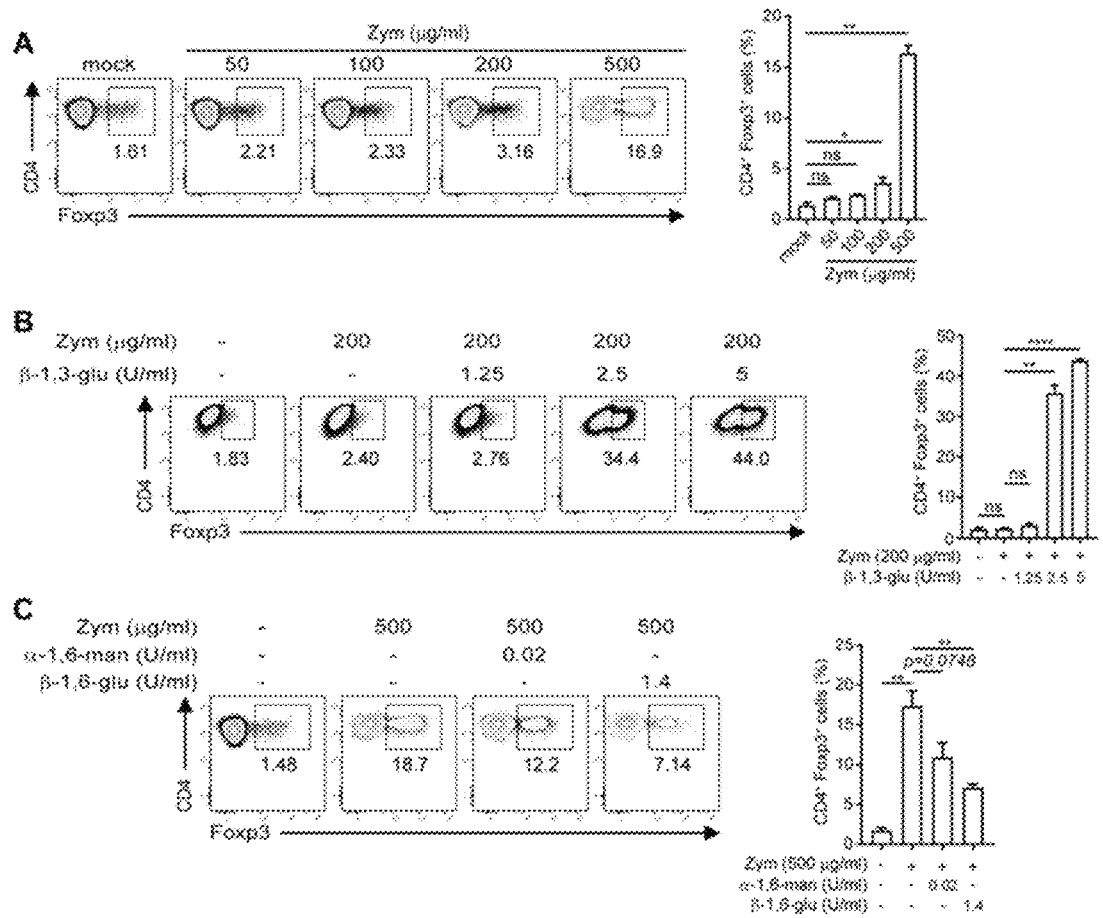
FIG. 1 shows a differential effect of a polysaccharide component derived from zymosan on the generation of Treg cells in vitro, wherein splenic CD11c+ DC was stimulated with a indicated dose of zymosan and then co-incubated with undifferentiated (naïve) CD4 T cells, flow cytometry plots represent three independent experiments, all data in graphs represent mean±SEM, * represents $p<0.05$,  represents $p<0.01$, * represents $p<0.001$, and **** represents $p<0.0001$ (Student's t-test).

In the same manner as in FIG. 1, splenic CD11c+ DC was treated with indicated molecules before co-incubation with naive CD4 T cells (FIGS. 5D and 5E).

FIG. 5D shows the frequency of CD4+Foxp3+ T cells induced by MGCP.

FIG. 5E shows the induction of Treg cells by MGCP cleaved with a indicated enzyme.

Flow cytometry plots represent three independent experiments with similar results, all data in graphs represent mean±SEM, * represents $p<0.05$,  represents $p<0.01$, * represents $p<0.001$, and **** represents $p<0.0001$ (Student's t-test).

Figure 6:
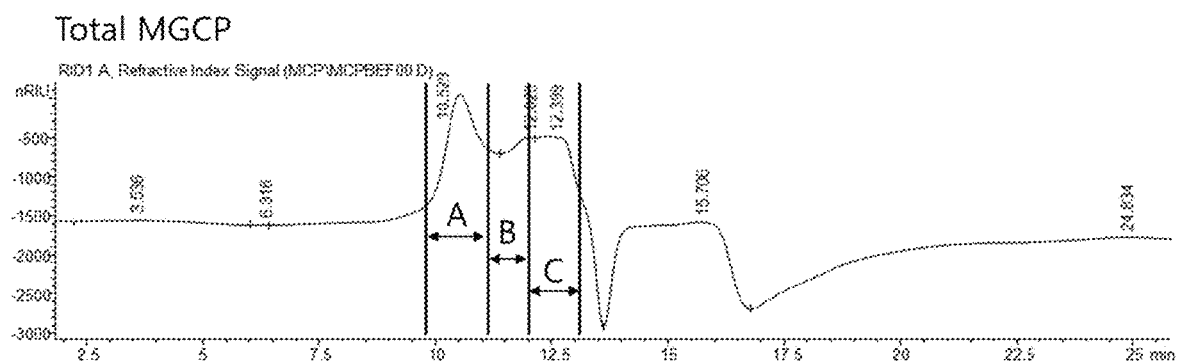

FIG. 6 shows the result of analysis of the entire MGCP using HPLC, wherein the HPLC analysis conditions were as follows: a TSK G-5000PWXL size exclusion column was used, the eluent was ammonium bicarbonate 50 mM, and the flow rate was 0.8 ml/min, the results of analysis were detected using a refractive index detector and a UV detector at a wavelength of 206 nm and the standard material used to detect the molecular weight was a dextran standard, and information thereon is shown in Table 2, and A, B and C represent the three fractions obtained through fractionation based on the results of HPLC analysis.

Figure 7:
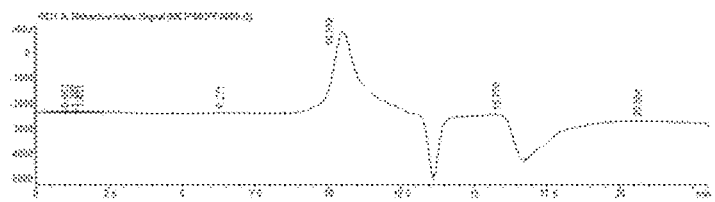
Figure 7:
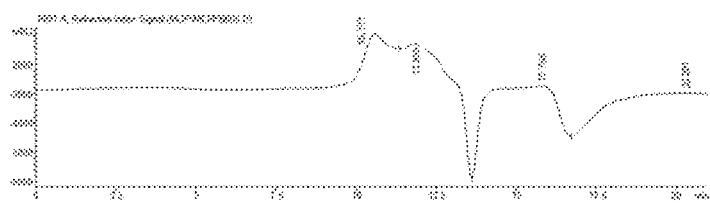
Figure 7:
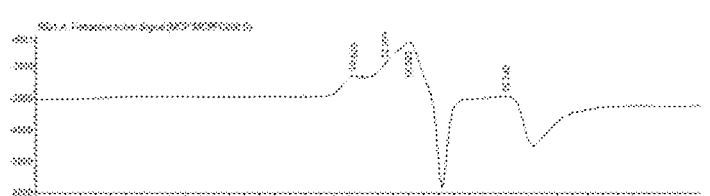

FIG. 7 shows the results of HPLC analysis of fractions A, B and C of MGCP in FIG. 6, wherein analysis was performed under the same conditions as in FIG. 6, the standard material used to detect the molecular weight was a dextran standard, and information thereon is shown in Table 2.

Figure 8:
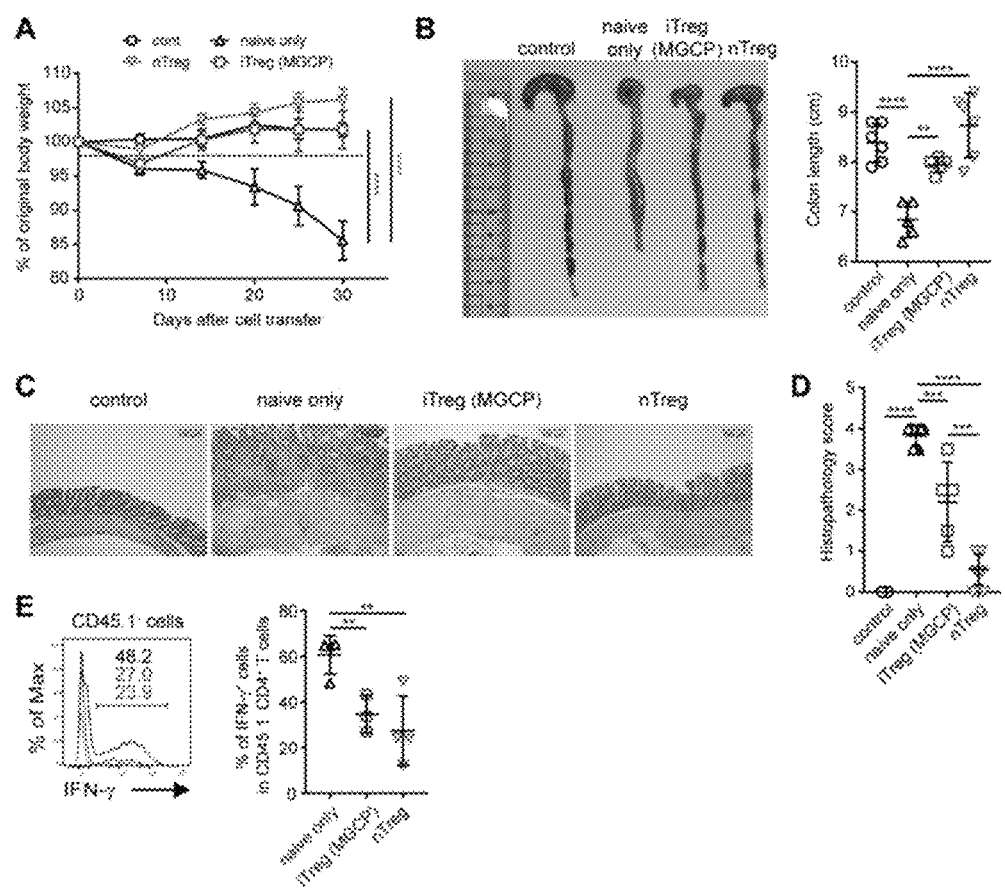

FIG. 8 shows the regulation of the inflammatory immune response of Treg cells induced by MGCP (in vivo). iTreg cells were produced by co-incubation of splenic DCs with naive CD4 T cells (CD45.1+CD4+Foxp3EGFP-CD44loCD62Lhi) marked congenically with splenic DCs in vitro, iTreg cells (CD45.1+CD4+Foxp3EGFP+) were selected FACs, and were adoptively transferred to Rag1−/− mice along with naive CD4 T cells (CD45.1-CD4+Foxp3Thy1.1CD44loCD62Lhi). Mice were analyzed at the endpoint. Each dot represents an individual mouse, and all data in bar graphs represent mean±SEM. * represents $p<0.05$,  represents $p<0.01$, * represents $p<0.001$, and **** represents $p<0.0001$ (Student's t-test).

FIG. 8A shows the change in body weight.

FIG. 8B is an image showing the length of the colon.

FIG. 8C is an image showing an H&E-stained colon.

FIG. 8D shows the histopathologic score of colitis.

FIG. 8E shows IFN-γ production in donor naive CD4 T cells (CD45.1-).

Figure 9:
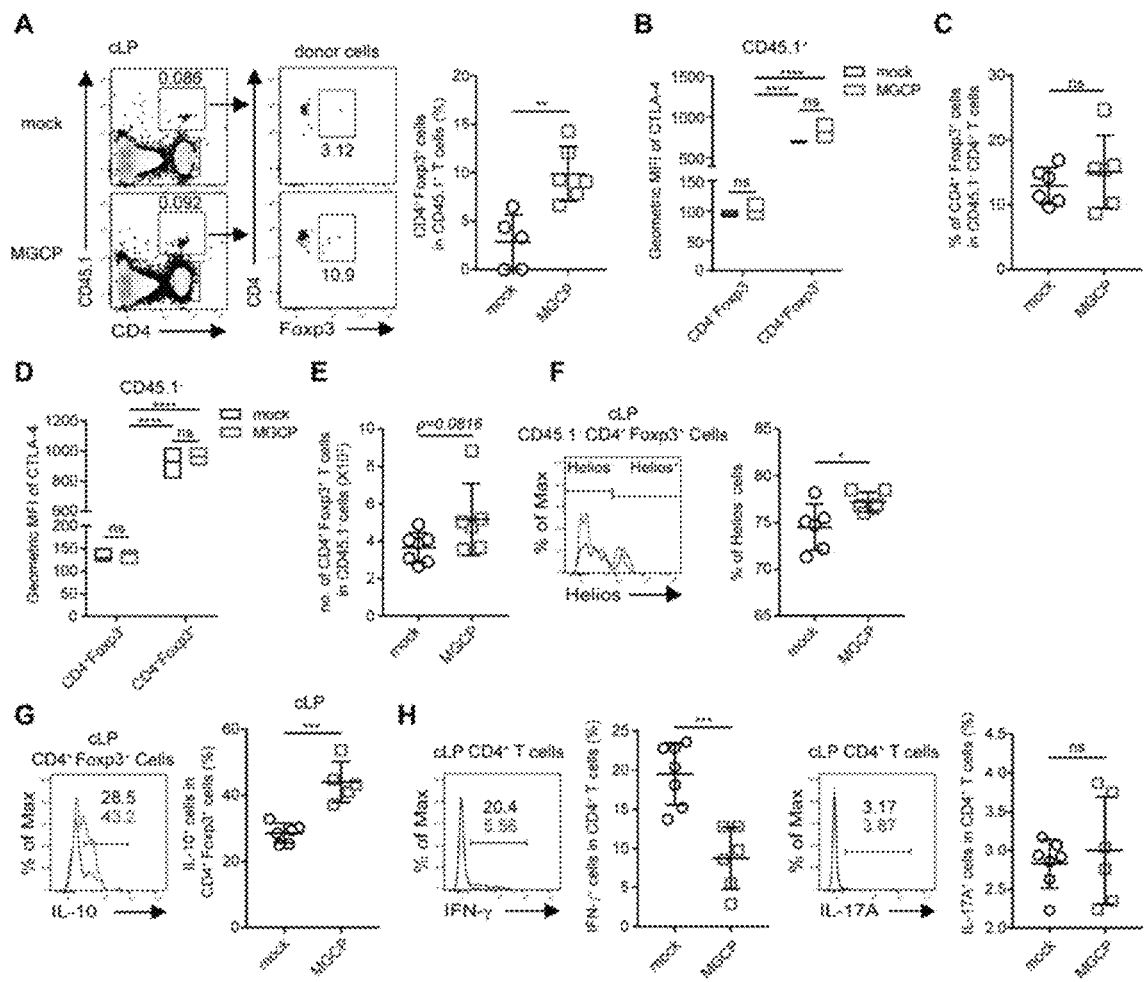

FIG. 9 shows that supplementation of MGCP in vivo promotes the generation of new Treg cells, wherein mice (CD45.1-) were treated with mock or 200 μg of MGCP daily for 2 weeks, and then received congenically-marked naive CD4 T cells (CD45.1+CD4+Foxp3EGFP-CD44loCD62Lhi), MGCP was further administered for one week after transfer of the cells, CD4 T cells were analyzed in the colonic lamina propria of recipient mice, each dot represents an individual mouse, flow cytometry plots represent independent experiments, all bar graphs represent mean±SEM, * represents $p<0.05$,  represents $p<0.01$, and * represents $p<0.001$ (Student's t-test).

FIG. 9A shows the frequency of Treg cells (CD45.1+CD4+Foxp3EGFP+) derived from donor cells.

FIG. 9B shows MFI of CTLA-4 in CD4+Foxp3EGFP- and CD4+Foxp3EGFP+ CD4 T cells derived from donor cells (CD45.1+).

FIG. 9C shows the frequency of Treg cells in recipient-derived cells (CD45.1-CD4+Foxp3EGFP+).

FIG. 9D shows the expression of CTLA-4 in host (CD45.1-)-derived CD4+Foxp3- cells and CD4+Foxp3+ cells.

FIG. 9E shows the number of recipient-derived Treg cells in the colonic lamina propria.

FIG. 9F shows the frequency of peripheral Treg cells in host-derived Treg cells (CD45.1−CD4+Foxp3EGFP+Helios−).

FIG. 9G shows the production of IL-10 from colon Treg cells (CD4+Foxp3EGFP+).

FIG. 9H shows the amounts of IFN-γ and IL-17A in effector CD4 T cells (CD4+Foxp3EGFP−).

Figure 10:
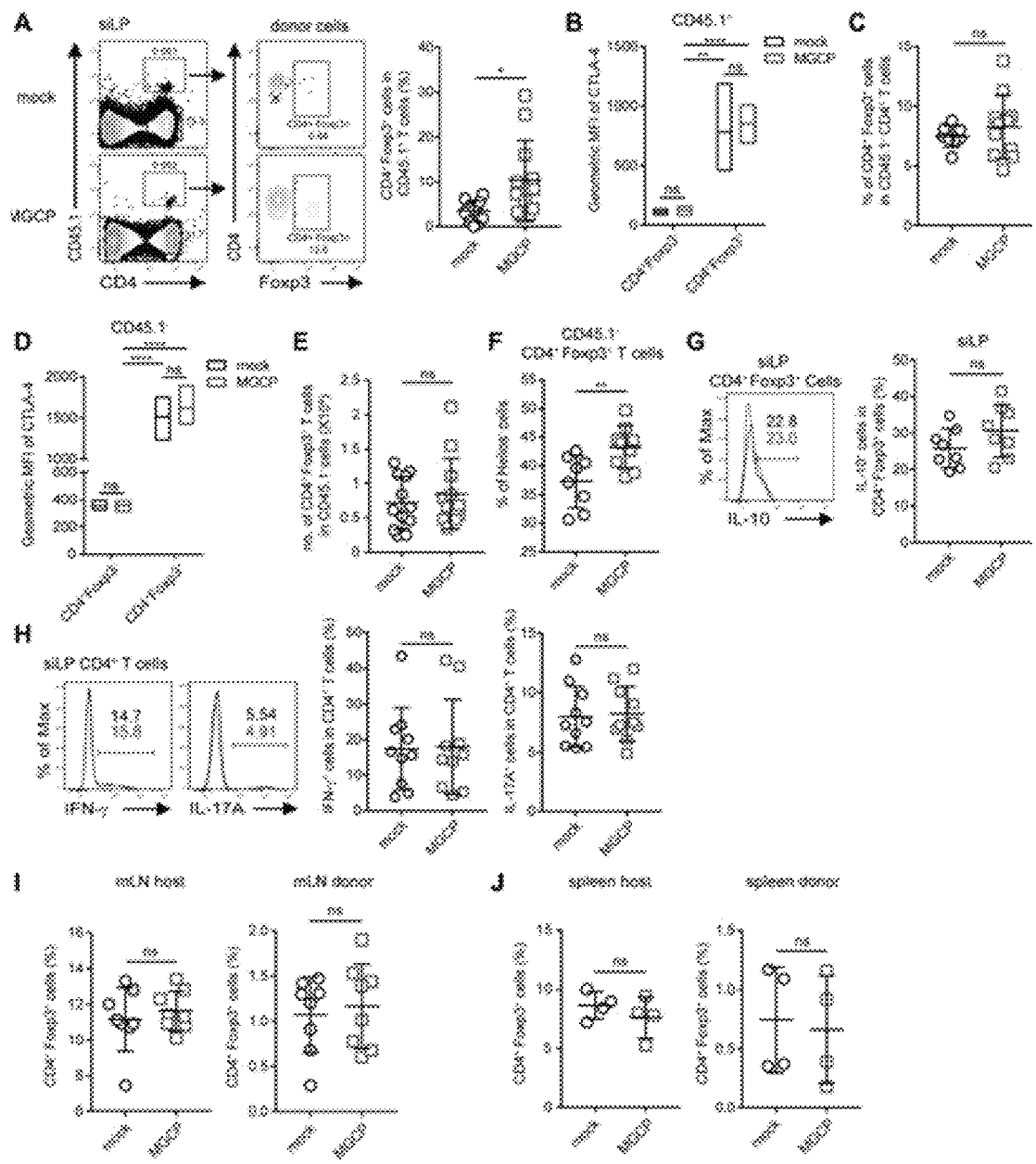

FIG. 10 shows that supplementation of MGCP induces Treg cells in the small intestine, but does not induce Treg cells in the lymph node tissue. In the same manner as shown in FIG. 9, MGCP (200 μg) was administered daily for 2 weeks, and then received congenically marked naive CD4 T cells. MGCP supplementation was continued for an additional week. CD4 T cells in the mucous membrane of the small intestine were evaluated (A-H). Each dot represents an individual mouse. Flow cytometry plots are representative of three independent experiments with similar results. All data in bar graphs represent mean±SEM. * represents p<0.05,  represents p<0.01, and * represents p<0.001 (Student's t-test).

FIG. 10A shows the differentiation from donor cells to CD4+Foxp3+ T cells.

FIG. 10B shows CTLA-4 expression from donor-derived CD4 T cells.

FIG. 10C shows the frequency of CD4+Foxp3+ T cells in receptor cells.

FIG. 10D shows the MFI of CTLA-4 in host-derived CD4 T cells.

FIG. 10E shows the number of CD4+Foxp3+ T cells in the mouse colon.

FIG. 10F shows the proportion of inducible Treg cells in recipient-derived CD4+Foxp3+ T cells.

FIG. 10G shows the production of IL-10 in CD4+Foxp3+ T cells.

FIG. 10H shows the production of IFN-γ and IL-17A in effector CD4 T cells (CD4+Foxp3−).

FIG. 10I shows CD4+Foxp3+ T cells derived from receptor and donor cells in mLN.

FIG. 10J shows CD4+Foxp3+ T cells derived from receptor and donor cells in the spleen.

Figure 11:
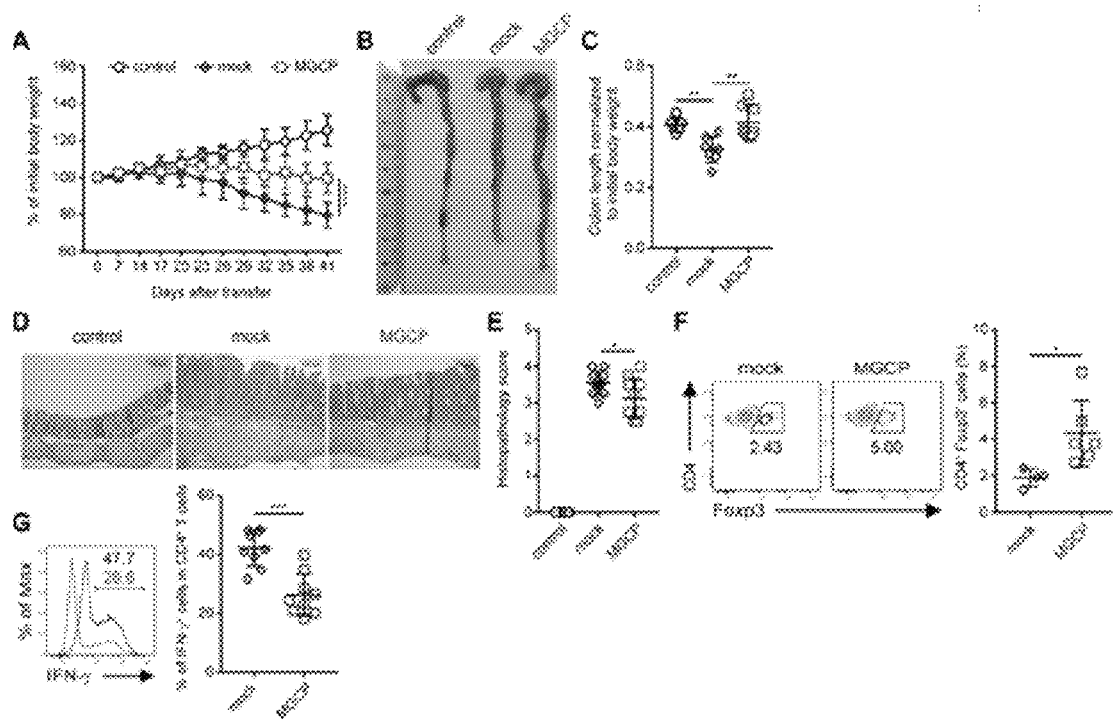

FIG. 11 shows that administration of MGCP induces antigen-reactive Treg cells and relieves experimental colitis. Naive CD4 T cells (CD4+Foxp3EGFP-CD44loCD62Lhi) isolated from CBir mice were adoptively transferred to Rag1-deficient mice. Throughout the experiment, DW (mock) or 200 μg of MGCP was supplemented every other day from the day before cell adoptive transfer. Receptors were analyzed at the endpoint. Mice were analyzed at the endpoint. Each dot represents an individual mouse. Data are representative of three independent experiments. All data in bar graphs represent mean±SEM, * represents p<0.05,  represents p<0.01, and * represents p<0.001 (Student's t-test).

FIG. 11A shows the change in body weight.

FIG. 11B is a representative image showing the colon.

FIG. 11C shows a normal colon length at an initial body weight.

FIG. 11D is an image showing an H&E-stained colon.

FIG. 11E shows the histopathologic score of colitis.

FIG. 11F shows results of analysis of the induction of CD4+Foxp3+ T cells from the colonic lamina propria in the early stage of weight loss.

FIG. 11G shows production of IFN-γ from colonic CD4 T cells (CD4+Foxp3EGFP−) at the endpoint of the experiment.

Figure 12:
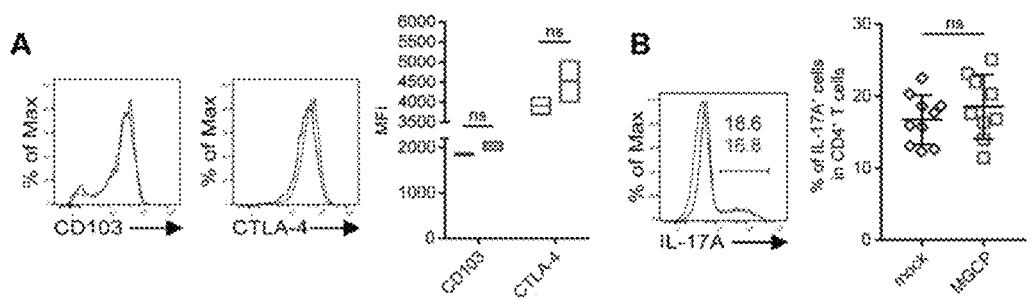

FIG. 12 shows the effect of administration of MGCP on immunity in the state of affliction with colitis.

FIG. 12A shows the expression levels of CD103 and CTLA-4 in Rag1-deficient mice that were administered with mock and MGCP, and received colon CD4+Foxp3+ T cells before weight loss.

FIG. 12B shows the production of IL-17A by CD4 T cells derived from the colonic lamina propria in the end stage of the experiment.

All data in bar graphs represent mean±SEM, * represents p<0.05,  represents p<0.01, and * represents p<0.001 (Student's t-test).

Figure 13:
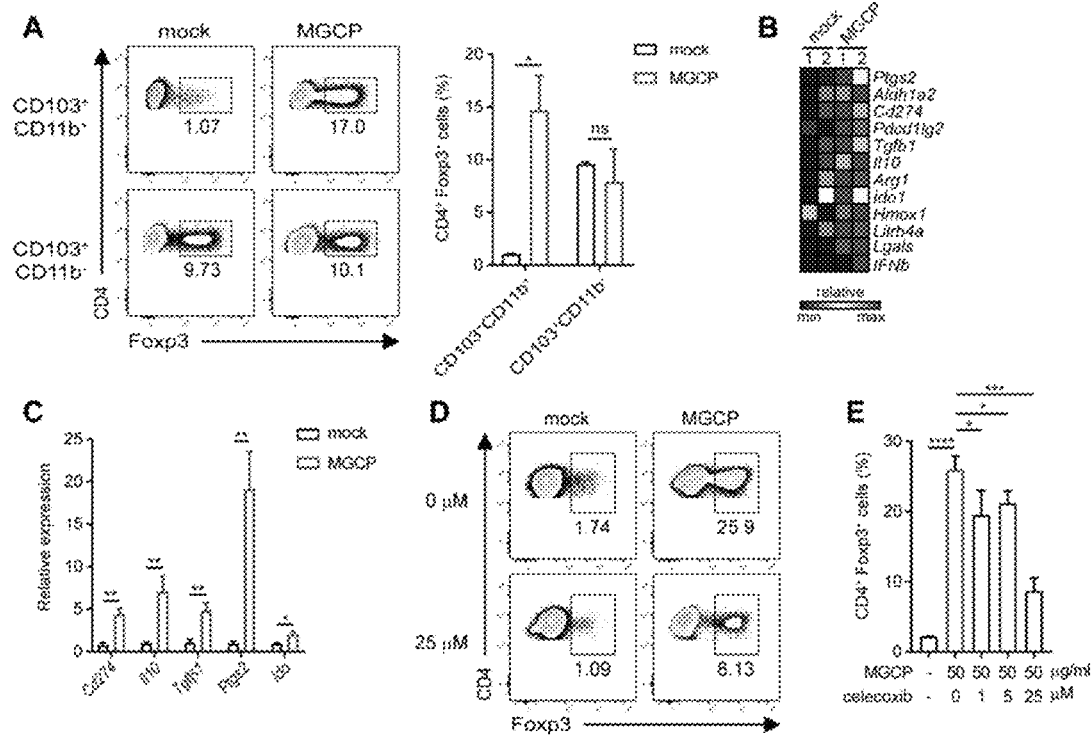

FIG. 13 shows that MGCP modulates the transcriptomic configuration of DC with respect to the regulatory phenotype. The DC subset (MHCII+CD11c+) is FACs classified from the small intestine according to the expression of CD103 and CD11b, and the ability of MGCP to induce Treg cells was tested using the same experimental procedure as in FIG. 1. Flow cytometry plots are representative of three independent experiments with similar results, and all data in bar graphs represent mean±SEM. * represents p<0.05,  represents p<0.01, and * represents p<0.001 (Student's t-test).

FIG. 13A shows data of MGCP-mediated induction of CD4+Foxp3+ T cells in each DC subset.

Mock or MGCP was administered to GF mice (n=6) for 2 weeks. Transcripts were purified from colon CD11c+ DC.

FIG. 13B shows immune-regulation-related markers in colon DC of GF mice administered with mock and MGCP.

FIG. 13C shows the expression of immunotolerant DC markers in colon DC.

Cox2 was inhibited in splenic DCs before treatment with MGCP and naive CD4 T cells were incubated with the DCs for 72 hours in the presence of celecoxib, a Cox2-selective inhibitor.

FIG. 13D shows flow cytometry plots of CD4+Foxp3+ T cells.

FIG. 13E shows the frequency of CD4+Foxp3+ T cells induced in the presence/absence of celecoxib and treated with mock or MGCP.

Figure 14:
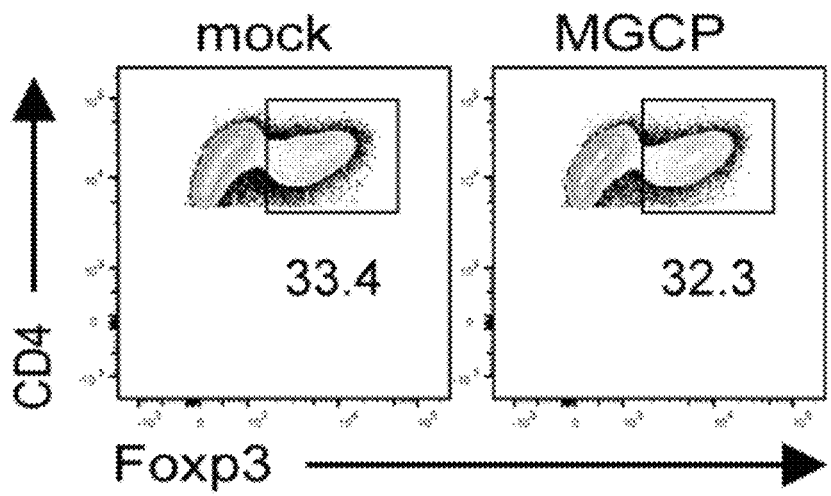

FIG. 14 shows the effect of intestinal macrophages on the generation of Treg cells by MGCP. Purified intestinal macrophages (MHCII+CD11c+CD11b+F4/80+CD103−) FACs were stimulated with MGCP before co-incubation with naive CD4 T cells. Flow cytometry plots are representative of two independent experiments with similar results.

Figure 15:
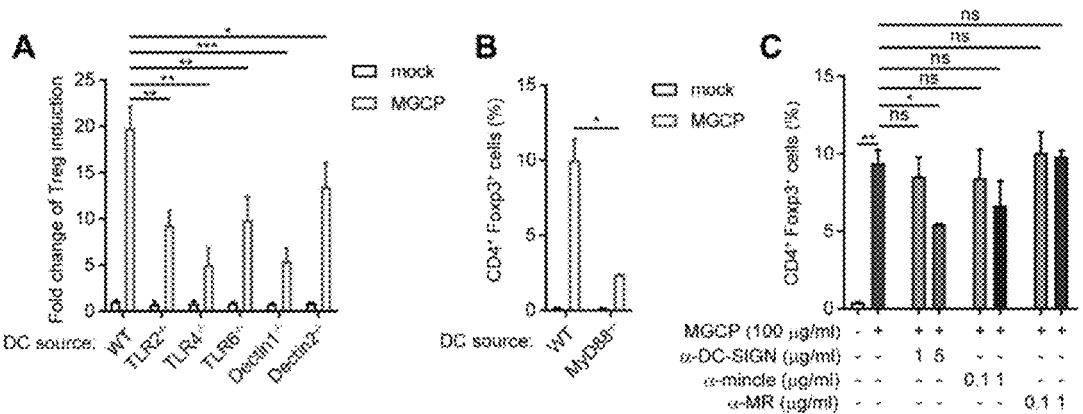

FIG. 15 shows the relationship between the generation of Treg cells induced by MGCP and various PRRs. Splenic DCs purified from specific innate immune-receptor-deficient mice were treated with MGCP in a manner similar to that shown in FIG. 1. Naive CD4 T cells were incubated with MGCP-stimulated DC.

FIG. 15A shows the frequency of CD4+Foxp3+ T cells when each receptor-deficient DC was treated with MGCP or mock.

FIG. 15B shows the frequency of CD4+Foxp3+ T cells when MyD88-signaling system-deficient DC was treated with MGCP or mock.

FIG. 15C shows the frequency of the generated CD4+Foxp3+ T cells. In FIG. 15C, certain CLRs were blocked with antagonists before spleen DCs were treated with MGCP. After washing off the remaining antagonists and MGCP, DC was co-incubated with naive CD4 T cells.

All data in bar graphs are mean±SEM, * represents p<0.05,  represents p<0.01, and * represents p <0.001 (Student's t-test).

Figure 16:
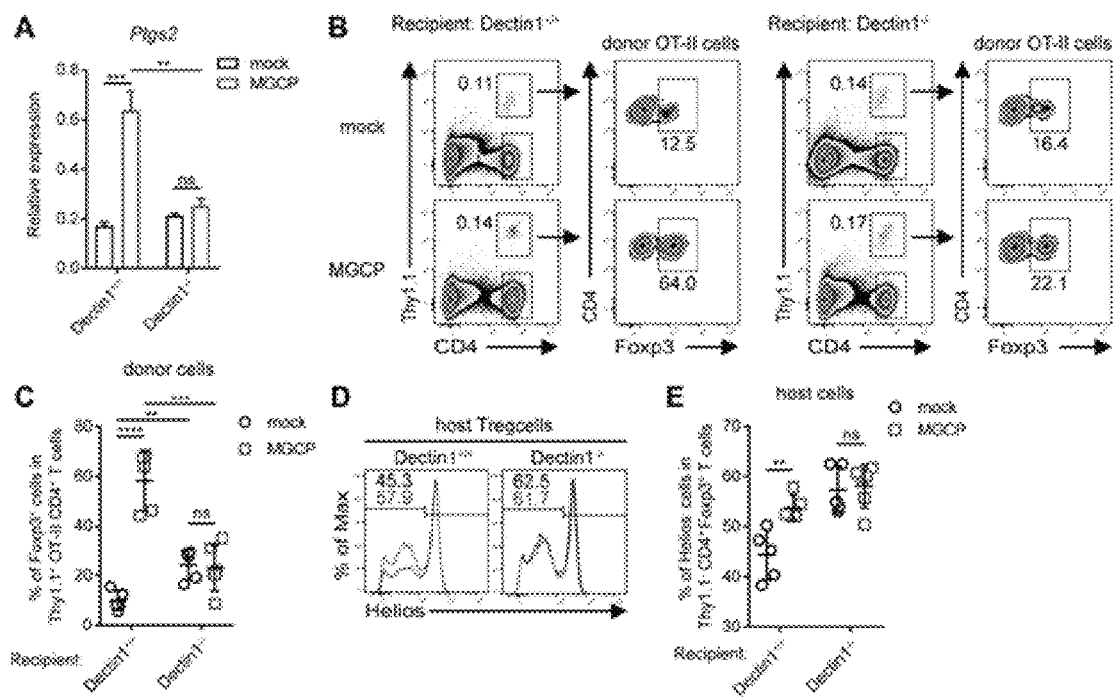

FIG. 16 shows the effect of Dectin1 on the induction of Treg cells by MGCP. The mesenteric lymph nodes CD11c+ DC of Dectin1-rich/deficient mice were stimulated with MGCP for 8 hours. Dectin1-damaged/intact mice were supplemented with 200 μg of MGCP daily for 2 weeks, and received "congenically" marked OT-II naive CD4 T cells (Thy1.1+Vα2+CD4+Foxp3EGFP−CD44loCD62Lhi). The receptors were administered with OVA protein (20 mg) every other day starting from the day before cell transfer, and at the same time, MGCP was further administered daily for one week.

FIG. 16A shows the expression of Cox2 transcript in DC treated with mock or MGCP.

FIG. 16B shows flow cytometry plots of Treg cells derived from donor OT-II CD4 T cells in the lamina propria of the small intestine.

FIG. 16C shows the frequency of Treg cells derived from donor OT-II CD4 T cells in the lamina propria of the small intestine.

FIG. 16D shows flow cytometry plots of the proportion of inducible Treg cells differentiated from receptor cells in the small intestine.

FIG. 16E shows the frequency of the proportion of inducible Treg cells differentiated from receptor cells in the small intestine.

Data are representative of three independent experiments with similar results. All data in bar graphs represent mean±SEM. * represents $p<0.05$,  represents $p<0.01$, * represents $p<0.001$ and **** represents $p<0.0001$ (Student's t-test).

Figure 17:
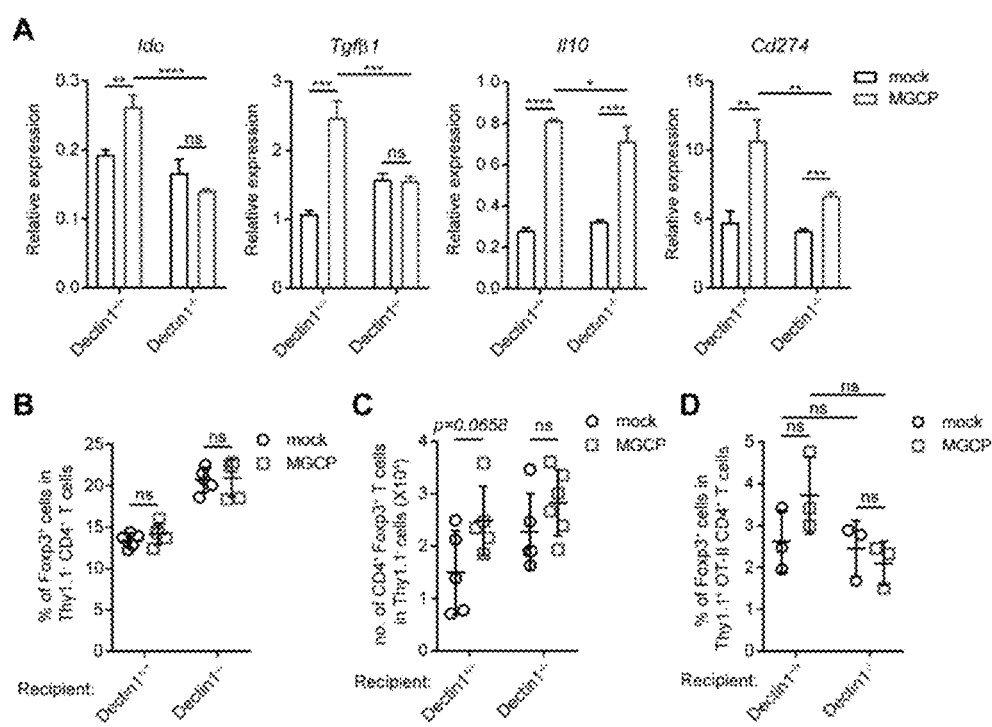

FIG. 17 shows that Dectin1 recognizes MGCP and induces the generation of Treg cells. The mesenteric lymph node CD11c+DC of Dectin1 rich/deficient mice was stimulated for 8 hours. In FIGS. 17B to 15D, before receiving OT-II naive CD4 T cells (Thy1.1+Vα2+CD4+Foxp3EGFP−CD44loCD62Lhi), Dectin1-damaged/intact mice were supplemented with 200 μg of MGCP daily for 2 weeks. OVA protein (20 mg/mouse) was administered every other day and MGCP was further administered for one week.

FIG. 17A shows the level of expression of indicated immunotolerant DC-related transcripts.

FIG. 17B shows the frequency of recipient-derived CD4+ Foxp3+ T cells in the small intestine.

FIG. 17C shows the number of recipient-derived CD4+ Foxp3+ T cells in the small intestine.

FIG. 17D shows the frequency of donor-derived OVA-reactive CD4+Foxp3+ T cells in mesenteric lymph nodes.

Each dot represents an individual mouse. Data are representative of three independent experiments with similar results. All data in bar graphs are mean±SEM. * represents $p<0.05$,  represents $p<0.01$, * represents $p<0.001$, and **** represents $p<0.0001$ (Student's t-test).

BEST MODE

Unless defined otherwise, all technical and scientific terms used herein have the same meanings as appreciated by those skilled in the field to which the present invention pertains. In general, the nomenclature used herein is well-known in the art and is ordinarily used.

Many studies have reported that zymosan can stimulate the pre-inflammatory immune response, and some results suggesting that zymosan plays a role in reducing immunity have been reported. However, the exact polysaccharide structure of the yeast that determines the immune response is still unknown.

In one embodiment of the present invention, the experimental data of zymosan showed that a large amount (500 μg/mL) promotes the differentiation of Treg cells, but that a low dose (50 μg/mL) promotes the expression of RORγt instead, and does not promote differentiation of Treg. In addition, it was found that beta-1,6-glucan and mannan, among components of polysaccharide, promote the differentiation of Treg cells and that beta-1,3-glucan inhibits the differentiation of Treg cells.

In another embodiment of the present invention, novel polysaccharides comprising mannan and beta-glucan, which are Treg cell-inducing components identified by the present inventors in the embodiment, were purified from the cell wall of yeast and called the same "mannan/β-glucan-comprising polysaccharides (MGCPs)", and it was found that Treg cells can be effectively induced even by treatment or administration of a low concentration of the polysaccharide in vitro and in vivo. Accordingly, a mechanism for differentiation of Treg cells based on the configuration and structure of a novel polysaccharide derived from the yeast cell wall was established in connection with receptors, gene transcript morphology change and cytokine expression, and administration of the polysaccharide or Treg cells induced thereby was found to effectively inhibit colitis in vivo.

In one aspect, the present invention is directed to a polysaccharide comprising mannan and beta-glucan (β-glucan).

In the present invention, the polysaccharide may have a structure in which mannan having an α-1,6-linked mannose backbone is bound to beta-glucan (β-glucan) having a β-1,6-linked glucose backbone.

In one embodiment of the present invention, as a result of structural/functional analysis of a novel polysaccharide (MGCP) derived from yeast, a specific binding structure between mannan and beta-glucan was identified and it was found that the beta-1,6-glucan backbone and mannan promote the differentiation of Treg cells, and that beta-1,3-glucan inhibits the differentiation of Treg cells.

In an embodiment of the present invention, it was found that the polysaccharide has a composition ratio of mannose (80.6%): glucose (14.9%): galactose (4.5%). The detailed structure of the mannan unit was found to have an alpha-1,6-linked mannose backbone, and to be connected with a single-unit mannose (30%), two-unit mannose (16.8%) or three-unit mannose (28.4%) as a side chain through alpha-1,2-linkage or alpha-1,3-linkage (mannose without a side chain (24.8%)) (FIG. 5B).

In the present invention, the polysaccharide may comprise mannose, glucose and galactose at a content ratio of 80.5%: 15.0%: 4.5%, specifically, 80.6%: 14.9%: 4.5%, more specifically 79.4%: 14.7%: 4.4%, but the present invention is not limited thereto.

Therefore, in the present invention, the polysaccharide may comprise mannose and glucose at a content ratio of 70% to 90%: 10% to 30%. In some cases, the polysaccharide may further comprise galactose in an amount of more than 0% and less than 10%.

In the present invention, the mannan comprises i) an alpha-1,6-linked mannose backbone and ii) as a side chain, at least one selected from the group consisting of alpha-1,2-linked or alpha-1,3-linked single-unit mannose, alpha-1,2-linked or alpha-1,3-linked two-unit mannose and alpha-1,2-linked or alpha-1,3-linked three-unit mannose. Specifically, the mannan may comprise i) an alpha-1,6-linked mannose backbone and ii) alpha-1,2-linked or alpha-1,3-linked single-unit mannose, two-unit mannose and three-unit mannose as side chains.

In the present invention, the polysaccharide may comprise the single-unit mannose side chain, the two-unit mannose side chain, the three-unit mannose side chain, and the mannose backbone having no side chain at a content ratio of 20% to 40%: 10% to 30%: 20% to 40%: 20% to 40%.

Specifically, the mannan of the polysaccharide may comprise 30% of the single-unit mannose, 17.0% of the two-unit mannose and 28.5% of the three-unit mannose, specifically, 30% of the single-unit mannose, 16.8% of the two-unit mannose and 28.4% of the three-unit mannose, and more specifically, 25.7% of the single-unit mannose, 22.6% of the two-unit mannose and 27.0% of the three-unit mannose, but is not limited thereto.

In one embodiment of the present invention, the mannan has a composition of 30% of the single-unit mannose, 16.8% of the two-unit mannose and 28.4% of the three-unit mannose.

In addition, in the present invention, the beta-glucan (β-glucan) comprises a β-1,6-linked glucose backbone and a β-1,3-linked single-unit glucose as a side chain. Preferably, the proportion of the beta-1,3-linked glucose side chain with respect to the total glucose may be 20.0%, specifically 18.0%, but is not limited thereto. In an embodiment of the present invention, it was found that the beta-glucan (β-glucan) comprises the beta-1,3-linked glucose side chain in an amount of 18% with respect to the total glucose.

In the present invention, it was found that beta-1,6-glucan and mannan promote the differentiation of Treg cells, and that beta-1,3-glucan inhibits the differentiation of Treg cells. Therefore, the beta-glucan may be composed of only beta-1,6-linked glucose, without beta-1,3-linked glucose.

In an embodiment of the present invention, as a result of detecting the molecular weight of a novel polysaccharide (MGCP) derived from yeast, two broad peaks were identified, and the molecular weight of the polysaccharide was detected to be about 4 kDa to 60 kDa. As a result of detection of three large fractions divided from the total polysaccharide, the polysaccharide was observed to have a molecular weight of about 3.5 kDa to 60 kDa. In addition, when the molecular weight of the polysaccharide is small, preferably 20 kDa or less, the Treg-inducing activity is excellent, whereas when the molecular weight of the polysaccharide is larger than 100 kDa, the Treg-inducing activity is deteriorated.

Therefore, in the present invention, the polysaccharide may have a molecular weight of 3.5 kDa to 60 kDa, and may preferably have a molecular weight of 4 kDa to 20 kDa.

In the present invention, the polysaccharide may induce the production of regulatory T cells (Treg), and the regulatory T cells are preferably CD4+Foxp3+ regulatory T cells, but are not limited thereto.

As used herein, the term "regulatory T cells (Treg)" is a type of differentiated T cells, and functions to regulate the immune function to thereby maintain tolerance to autoantigens and regulate the onset of autoimmune diseases. Regulatory T cells generally express immunosuppressive cytokines such as IL-10, and inhibit the induction and proliferation of effector T cells.

As used herein, the term "induction" means induction of differentiation or production of desired cells, and in the present invention, is used to indicate the differentiation of naive T cells into regulatory T cells.

In the present invention, the term "induction" can be used interchangeably with "differentiation", "generation", "production" or the like.

As used herein, the term "naive T cell" refers to a pre-differentiated T cell before a progenitor T cell in the thymus gland matures in the bone marrow. Naive T cells may be differentiated into effector T cells, helper T cells (Th), regulatory T cells (Treg), and the like upon stimulation with IL-2, IL-4 and TGF-β.

In the present invention, the induction of the regulatory T cells may be mediated by dendritic cells (DCs), and the DCs may express pattern recognition receptors (PRRs). The pattern recognition receptors may preferably comprise at least one selected from the group consisting of Dectin1, Dectin2, TLR2, TLR4 and TLR6, but are not limited thereto.

In the present invention, the mediation by DC may comprise mediation of the induction of Treg cells by modification of the transcriptome landscape to tolerogenic DC based on simulation through treatment with the polysaccharide. Preferably, the modification of the transcriptome landscape may be overexpression of at least one selected from the group consisting of IL-10, Cd274, indoleamine 2,3-dioxygenase (IDO), Tgfβ1 and Cox2 (cyclooxygenase-coding gene, Ptgs2), but is not limited thereto.

In addition, in the present invention, the polysaccharide may improve the expression of Helios, IL-10 and CTLA-4 from Treg, and may reduce IFN-γ of effector T cells.

In one embodiment of the present invention, the novel polysaccharide was derived from yeast extract, and was specifically isolated from the cell wall of yeast. The mannan/beta-glucan-comprising polysaccharide (MGCP) derived from the yeast cell wall from which beta-1,3-glucan was removed exhibited increased Treg cell induction ability.

In the present invention, the polysaccharide may be derived from yeast, may preferably be derived from a yeast cell wall, and may more preferably be derived from the cell wall of yeast from which beta-1,3-glucan has been removed.

In the present invention, the polysaccharide preferably has activity of modulating an anti-inflammatory function or an immune function, more preferably an immunosuppressive activity, but is not limited thereto. For example, patients with intestinal wounds such as intestinal bleeding may suffer from side effects when incorrectly administered with probiotics. In this case, therapeutic effects can be obtained through administration of polysaccharides.

In another aspect, the present invention is directed to a composition for immunomodulation comprising the polysaccharide as an active ingredient.

As used herein, the term "immunomodulation" means resolving an immune imbalance in the blood and maintaining immune homeostasis. Maintenance of immune homeostasis refers to a state in which the balance between immune tolerance, which regulates immunity and immune response which promotes immunity, is acquired. Maintaining this state is essential for the treatment of immune diseases, particularly the treatment of autoimmune diseases.

The composition for immunomodulation may be used as a pharmaceutical composition or a health functional food for regulating immune activity and preventing, ameliorating or treating immune diseases, and the amount and form that is used may be appropriately adjusted according to the purpose.

In one embodiment of the present invention, it was found that oral administration of MGCP increases the induction of colon Treg cells. In addition, oral administration of MGCP significantly increased the expression of CTLA-4 and IL-10 in Treg cells, and remarkably reduced IFN-γ expression in effector T cells.

In another embodiment of the present invention, in mice with microbial flagellin-reactive CD4 T cells fed with MGCP, weight loss and shortening of colon length were remarkably reduced, and proliferation of epithelial cells and penetration of lymphocytes into the colon were also effectively inhibited. Histopathology scoring also showed remarkable alleviation compared to mock-administered mice.

In another aspect, the present invention is directed to a pharmaceutical composition for preventing and treating an immune disease or inflammatory disease comprising the polysaccharide as an active ingredient.

As used herein, the term "immune disease" refers to a disease that may be directly caused by an abnormality in the immune system, and may be selected from the group consisting of dermatitis, allergies, rhinitis, gout, ankylosing spondylitis, rheumatic fever, lupus, fibromyalgia, tendonitis, type 1 diabetes, scleroderma, neurodegenerative disease, type 2 diabetes, silicosis, atherosclerosis, vitiligo, conjunctivitis, and autoimmune disease, but is not limited thereto.

As used herein, the term "autoimmune disease" refers to a disease that occurs when immune cells in an organism recognize the organism's own tissues or cells, rather than an external invading antigen, as an antigen and attack the same. The autoimmune disease may be selected from the group consisting of rheumatoid arthritis, systemic scleroderma, atopic dermatitis, psoriasis, asthma, Guillain-Barre syndrome, myasthenia gravis, dermatomyositis, polymyositis, multiple sclerosis, autoimmune encephalomyelitis, polyarteritis nodosa, temporal arteritis, childhood diabetes, alopecia areata, blisters, aphthous stomatitis, Crohn's disease, and Behcet's disease, but is not limited thereto.

As used herein, the term "inflammatory disease" is a generic term for a disease accompanied by inflammation as a main lesion, particularly one selected from the group consisting of edema, allergies, asthma, conjunctivitis, periodontitis, rhinitis, otitis media, sore throat, tonsillitis, pneumonia, gastric ulcer, gastritis, Crohn's disease, colitis, hemorrhoids, gout, ankylosing spondylitis, rheumatic fever, lupus, fibromyalgia, psoriatic arthritis, osteoarthritis, rheumatoid arthritis, periarthritis of the shoulder, tendinitis, tenosynovitis, myositis, hepatitis, cystitis, nephritis, Sjogren's syndrome, severe myasthenia gravis, and multiple sclerosis, but is not limited thereto.

As used herein, the term "prevention" or "prophylactic" refers to any action that can regulate or delay the onset of an immune disease or inflammatory disease by administration of the pharmaceutical composition according to the present invention.

As used herein, the term "treatment" or "therapeutic" refers to any action that can ameliorate or beneficially alter the symptoms of an immune disease or inflammatory disease by administration of the pharmaceutical composition according to the present invention.

The pharmaceutical composition of the present invention exhibits a prophylactic or therapeutic effect for various immune diseases and an anti-inflammatory effect based on the immunity-enhancing effect or hyper-immunity regulation effect of the active ingredient.

In addition to the polysaccharide, the pharmaceutical composition may further comprise a suitable carrier, excipient and diluent which are commonly used in pharmaceutical compositions.

Examples of the carrier, excipient and diluent that may be comprised in the pharmaceutical composition may comprise lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil and the like. Upon formulation of the composition, typically used diluents or excipients, such as fillers, extenders, binders, wetting agents, disintegrants or detergents, may be used.

The pharmaceutical composition according to the present invention can be formulated and used in various forms according to a conventional method. Suitable formulations comprise oral formulations such as tablets, pills, powders, granules, sugar-coated tarblets, hard or soft capsules, solutions, suspensions, emulsions, injections and aerosols, external preparations, suppositories, sterile injectable solutions, and the like, but are not limited thereto.

The pharmaceutical composition according to the present invention can be prepared into a suitable formulation using a pharmaceutically inactive organic or inorganic carrier. That is, when the formulation is a tablet, a coated tablet, a sugar-coated tarblets or a hard capsule, it may comprise lactose, sucrose, starch or a derivative thereof, talc, calcium carbonate, gelatin, stearic acid, or a salt thereof. In addition, when the formulation is a soft capsule, it may comprise a vegetable oil, wax, fat, or semi-solid or liquid polyol. In addition, when the formulation is in the form of a solution or syrup, it may comprise water, polyol, glycerol, vegetable oil, or the like.

The pharmaceutical composition according to the present invention may further comprise a preservative, a stabilizer, a wetting agent, an emulsifier, a solubilizing agent, a flavoring agent, a colorant, an osmotic pressure regulator, an antioxidant or the like, in addition to the above carrier.

The pharmaceutical composition according to the present invention may be administered in a pharmaceutically effective amount, and the term "pharmaceutically effective amount" refers to an amount sufficient for treating a disease at a reasonable benefit/risk ratio applicable to all medical treatments, and the effective dosage level may be determined depending on a variety of factors comprising the type of the disease of the patient, the severity of the disease, the activity of the drug, the sensitivity of the patient to the drug, the administration time, the administration route, the excretion rate, the treatment period, drugs used concurrently therewith, and other factors well-known in the pharmaceutical field. The pharmaceutical composition of the present invention may be administered as a single therapeutic agent or in combination with other therapeutic agents, may be administered sequentially or simultaneously with a conventional therapeutic agent, and may be administered in one or multiple doses. Taking into consideration these factors, it is important to administer the minimum amount sufficient to achieve maximum efficacy without side effects, and the amount can be easily determined by those skilled in the art.

The composition of the present invention may be administered in combination with an immunity-related protein, particularly an autoimmune or allergy-related protein. Specifically, examples of such proteins comprise autoantigens involved in autoimmune diseases, for example, heat shock proteins (HSPs), citrullinated filaggrin, glucose-6-phosphate isomerase, p205, collagen, and the like for rheumatoid arthritis, insulin, zinc transporter 8 protein (ZnT8), pancreatic and duodenal homeobox 1 (PDX1), Chromogranin A (CHGA), islet amyloid polypeptide (IAPP), and acetylcholine receptors, which are autoantigens related to myasthenia gravis. In addition, such proteins comprise not only all kinds of autoantigens known to cause autoimmune diseases, but also various allergens known to cause food allergies, such as peanuts, milk, eggs, tree nuts, soybeans, crustaceans such as shrimp, substances derived from fish and the like.

The pharmaceutical composition according to the present invention may be administered to a subject by various routes. The mode of administration may be, for example, subcutaneous, intravenous, intramuscular, intrauterine dural, or cerebrovascular injection. The pharmaceutical composition of the present invention is determined according to the type of drug as the active ingredient, as well as various related factors such as the type of the disease to be treated, the route of administration, the age, gender and weight of the patient, and the severity of the disease.

The method of administering the pharmaceutical composition according to the present invention may be easily selected depending on the formulation, and the pharmaceutical composition may be administered orally or parenterally. The dosage may vary depending on the age, gender and weight of the patient, the severity of the disease, and the route of administration.

In another aspect, the present invention is directed to a method of preventing or treating an immune disease or inflammatory disease comprising administering the polysaccharide of the present invention or the composition comprising the polysaccharide as an active ingredient to a subject.

In another aspect, the present invention is directed to the use of the polysaccharide of the present invention or the composition comprising the polysaccharide for the prevention or treatment of an immune disease or inflammatory disease.

In another aspect, the present invention is directed to the use of the polysaccharide of the present invention for the preparation of a drug for preventing or treating an immune disease or inflammatory disease.

The pharmaceutical composition according to the present invention not only provides excellent regulation effects of immunity-enhancing and hyperimmunity effects, but also has almost no toxicity and side effects such as those typically caused by drugs, and thus may be administered for a long time for the purpose of treatment or prevention of immune diseases.

In another aspect, the present invention is directed to a food for preventing or ameliorating an immune disease or inflammatory disease comprising the polysaccharide as an active ingredient.

The food for preventing or ameliorating an immune disease or inflammatory disease may be a health functional food that has activity of maintaining homeostasis of immune functions by enhancing immune activity, or regulating or alleviating hyperimmunity.

The term "food" comprises meat, sausage, bread, chocolate, candy, snacks, confectioneries, pizza, ramen, other types of noodles, gum, dairy products comprising ice cream, various soups, beverages, teas, drinks, alcoholic beverages, vitamin complexes, health functional foods and health foods and the like, and encompasses any general food.

The term "functional food" has the same meaning as the term "food for special health use (FoSHU)" and refers to a food having strong medical and pharmaceutical effects that has been processed to efficiently provide a bioregulatory function as well as a nutrition supply function. Here, the term "functional" means obtaining beneficial effects for health purposes, such as controlling nutrients or exhibiting physiological effects with regard to the structures and functions of the human body. The food of the present invention may be prepared by a method commonly used in the art, and the preparation may be performed using raw materials and ingredients commonly added in the art. In addition, the food may also be prepared into any formulation recognized as a food without limitation, and the health functional food according to the present invention may be in the form of a powder, granule, tablet, capsule, or beverage.

The term "health food" refers to a food having an active health maintenance or promotion effect beyond that of a general food, and "health supplement food" refers to a food ingested for the purpose of health improvement. In some cases, the terms "health functional food", "health food", and "health supplement food" are used interchangeably.

The food composition may further comprise a physiologically acceptable carrier, and there is no particular limitation as to the kind of carrier, and any carrier commonly used in the art may be used.

In addition, the composition may comprise additional ingredients that are commonly used in food compositions to improve smell, taste, visual quality (appearance), and the like. For example, the composition may comprise vitamins A, C, D, E, B1, B2, B6 and B12, niacin, biotin, folate, pantothenic acid, and the like. In addition, minerals such as zinc (Zn), iron (Fe), calcium (Ca), chromium (Cr), magnesium (Mg), manganese (Mn), copper (Cu), and chromium (Cr) may be comprised. In addition, amino acids such as lysine, tryptophan, cysteine, and valine may be comprised.

In addition, the composition may comprise food additives such as preservatives (potassium sorbate, sodium benzoate, salicylic acid, sodium dehydroacetate, etc.), disinfectants (bleached powder and highly bleached powder, sodium hypochlorite, etc.), antioxidants (butylhydroxyanisole (BHA), butylhydroxytoluene (BHT), etc.), colorants (tar color, etc.), color-developing agents (sodium nitrite, sodium nitrite, etc.), bleaching agents (sodium sulfite), seasonings (MSG, etc.), sweeteners (dulcin, cyclamate, saccharin, sodium, etc.), flavorings (vanillin, lactones, etc.), expanding agents (alum, D-potassium hydrogen tartrate, etc.), reinforcing agents, emulsifiers, thickeners, coating agents, gum base agents, foaming inhibitors, solvents, and improving agents. The additive may be selected according to the type of food and used in an appropriate amount.

In addition to the polysaccharide of the present invention, the composition may further comprise a foodologically acceptable food supplement additive, may be used in combination with other foods or food ingredients, and may be appropriately used according to a conventional method. The amount of the active ingredient that is mixed may be appropriately determined according to the purpose of use (prevention, health or therapeutic treatment).

In one embodiment of the present invention, it was found that MGCP induced colon Treg cells, increased the expression of IL-10 and CTLA-4 in Treg cells, and inhibited the expression of IFN-γ in effector T cells, both in vivo and in vitro, thereby inhibiting the immune function.

In another embodiment of the present invention, it was found that the polysaccharide mediates DC to induce Treg cells. Specifically, it was found that the cell differentiation of Treg was decreased when Dectin1, Dectin2, TLR2, TLR4 and TLR6 of DC were deficient, and that the reduction was remarkable, in particular, when Dectin1 and TLR4 were deficient. Also, it was found that the induction of Treg cells decreased even when the MyD88 signaling system was deficient.

In another embodiment of the present invention, the recognition of polysaccharide through PRR alters the transcriptome landscape of DCs such as IL-10, Cd274, indoleamine 2,3-dioxygenase (IDO), Tgfβ1 and Cox2, into a tolerogenic DC phenotype. In particular, as a result of an experiment after treatment with celecoxib, it was found that Cox2 was overexpressed, thereby inducing Treg cells. In addition to dendritic cells, Treg cells can be induced by any cell that recognizes and presents an antigen.

In another aspect, the present invention is directed to a method of producing regulatory T cells (Treg cells), the method comprising treating antigen-presenting cells with the polysaccharide according to the present invention, and then obtaining tolerogenic antigen-presenting cells; and co-incubating the tolerogenic antigen-presenting cells with CD4+ T cells, and then inducing regulatory T cells (Treg cells).

As used herein, the term "antigen-presenting cell" refers to a cell that induces differentiation by accepting and responding to an antigen and then presenting an antigen-derived fragment to a T cell together with an antigen-presenting molecule such as an MHC class II molecule. For example, the antigen-presenting cells comprise macrophages, B cells, dendritic cells (DC), and Langerhans cells, but are not limited thereto.

As used herein, the term "tolerogenic antigen presenting cell" refers to a type of antigen-presenting cell having an immunosuppressive property that makes the immune system tolerogenic to various antigens. Tolerogenic antigen-presenting cells mainly affect the immune environment through T cell regulation, such as induction of anergy and death of T cells, and induction of Treg cells. Due to these immunosuppressive properties, tolerogenic antigen-presenting cells have been spotlighted as candidate substances for use in cell therapy in response to allergy-related diseases and autoimmune diseases. The tolerogenic antigen-presenting cells may be, for example, tolerogenic macrophages, tolerogenic dendritic cells (DCs), or tolerogenic B cells, but are not limited thereto.

In the present invention, the antigen-presenting cells may express pattern recognition receptors (PRRs). The pattern recognition receptors preferably comprise one or more selected from the group consisting of Dectin1, Dectin2, TLR2, TLR4, and TLR6, but are not limited thereto.

In the present invention, the tolerogenic antigen-presenting cells overexpress one or more selected from the group consisting of IL-10, Cd274, indoleamine 2,3-dioxygenase (IDO), Tgfβ1 and Cox2, but are not limited thereto.

In the present invention, the regulatory T cells are preferably CD4+Foxp3+ regulatory T cells, but are not limited thereto.

In addition, in the present invention, the polysaccharide may increase the expression of Helios, IL-10, and CTLA-4 from Treg cells, and may reduce IFN-γ in effector T cells.

In one embodiment of the present invention, in order to determine whether or not MGCP-induced Treg cells have functional activity in vivo and can alleviate colitis, Treg cells (CD45+) produced by the MGCP-treated DCs were adoptively delivered to mice together with naïve CD4+ T cells. The weight loss and shortening of the colon length in the recipient mice were significantly reduced in the MGCP-Treg-receiving mice, and the destruction of the structure of epithelial cells in the colon tissue was prevented and the penetration of lymphocytes into the mucosa of the colon was inhibited, as can be seen from the histopathology score. In addition, the level of IFN-γ produced in donor naïve CD4+ T cells was remarkably reduced.

In another aspect, the present invention is directed to a cell therapeutic agent for preventing or treating an immune disease or inflammatory disease comprising the regulatory T cells (Treg cells) produced by the method as an active ingredient.

In another aspect, the present invention is directed to the use of the cell therapeutic agent for the prevention or treatment of an immune disease or an inflammatory disease.

In the present invention, the regulatory T cells are preferably CD4+Foxp3+ regulatory T cells, but are not limited thereto.

In another aspect, the present invention is directed to the use of the polysaccharide or the cell therapeutic agent for the preparation of a drug for preventing or treating an immune disease or an inflammatory disease.

Hereinafter, the present invention will be described in more detail with reference to examples. However, it will be obvious to those skilled in the art that these examples are provided only for illustration of the present invention and should not be construed as limiting the scope of the present invention.

Materials and Methods

1. Mouse

Mice were bred in an animal facility at the POSTECH Biotech Center. All experimental procedures were carried out with the approval of the Institutional Animal Care & Use Committee of POSTECH Laboratories. C57BL/6 mice were continuously inbred at POSTECH. Foxp3-eGFP, Tlr2−/−, Tlr4−/−, Tlr6−/− and MyD88−/− mice were obtained from Jackson Laboratory. CD45a-Rag1−/−TCR OT-II (Rag1−/− OTII TCR transformant) and Rag1−/− mice were obtained from Taconic Biosciences, Inc. Dectin1−/− and Dectin2−/− animals were provided by Dr. Yoichiro Iwakura (Tokyo University of Science, Japan). Germ-free (GF) C57BL/6 mouse colonies were established by breeders with the help of Dr. Andrew Macpherson (Bern Univ., Switzerland) and Dr. David Artis (Then at Univ. Pennsylvania, currently at Cornell Univ., USA). GF mice were kept in sterile flexible film isolators (Class Biological Clean Ltd., USA). CBir mice were provided by Charles O. Elson of the University of Alabama, Birmingham. 6 to 12 weeks old mice with suitable gender and age were used.

2. Purification of MGCP from Yeast Cell Wall 20 g of an yeast extract (BD Biosciences), 2 g of polysorbate 80 (Sigma-Aldrich), 4 g of ammonium citrate (Sigma-Aldrich), 10 g of sodium acetate (Sigma-Aldrich), magnesium sulfate (Sigma-Aldrich), 0.1 g of manganese sulfate (Sigma-Aldrich), and 4 g of dipotassium phosphate (Sigma-Aldrich) were dissolved in 2 L of distilled water. The solution was autoclaved and then cooled to room temperature. The solution was treated with trichloroacetic acid (TCA, Sigma Aldrich) to a final concentration of 0.4% and incubated at 4° C. with magnetic stirring overnight. The TCA-treated solution was incubated at −20° C. along with 3 drops of cooled ethanol overnight. The cultured solution was centrifuged, the supernatant was removed, and the pellet was then dried to remove the remaining ethanol and suspended in 10 mM Tris buffer containing 20 mM $MgCl_2$ and 20 mM $CaCl_2$ (pH 7.5). The suspended solution was treated with RNase (Sigma-Aldrich) and DNase (Roche) to a final concentration of 0.4 mg/ml and incubated overnight at 37° C. Then, the solution was treated with sodium azide to a final concentration of 0.05% and incubated at 37° C. for 30 minutes. After incubation, the result was treated with 0.3 mg/ml of a Pronase (protease, Streptomyces griseus, Sigma-Aldrich) solution and incubated at 37° C. overnight. Pronase was further added again to the solution to obtain the final concentration of 0.3 mg/mL, followed by further incubation for 2 hours. TCA was added to obtain a final concentration of 0.4%, followed by incubation at 37° C. for 2 hours. The solution was centrifuged and the supernatant was transferred to 3 drops of cooled ethanol and incubated at −20° C. overnight. After centrifugation, the supernatant was removed and the pellet was dried to remove residual ethanol. The pellet was suspended in 100 mM Tris buffer (pH 7.5), treated with the same amount of phenol, and inverted several times to thoroughly mix the same. The solution was centrifuged, and the upper tube was transferred to a fresh tube and repeatedly treated with phenol. The solution was centrifuged and the supernatant was transferred to a fresh tube and treated with the same amount of an isoamyl alcohol:chloroform 1:29 (v:v) solution, followed by thorough mixing. After centrifugation, the supernatant was transferred, and this process was repeated once more. Polysaccharides were obtained by dialysis in distilled water for 3 days followed by freeze-drying. The concentration of polysaccharides was measured by acidic phenol analysis.

3. Lymphocyte Isolation and Flow Cytometry Analysis

Naive CD4 T cells were obtained from pLN, mLN and spleen using a FACs sorter (Astrios, Beckman Coulter) or an EasySep™ mouse Naive® CD4+ T cell isolation kit (STEMCELL Technology) according to the manufacturer's protocol. In the isolation from the large intestine and small intestine, the intestine was incised vertically, opened, and washed with PBS to remove mucus and feces. A small section was cut from the intestine and then incubated at 37° C. for 20 minutes while being stirred with a magnetic bar using PBS containing 10 mM EDTA, 20 mM HEPES, 1 mM sodium pyruvate and 3% FBS. The tissue was crushed and incubated in RPMI 1640 medium supplemented with 3% FBS, 20 mM HEPES, 1 mM sodium pyruvate, 0.5 mg/ml Collagenase D (Roche) and DNase I (Sigma-Aldrich) at 37° C. for 45 minutes. The tissue was further incubated in the presence of 10 mM EDTA for 5 minutes. The supernatant was filtered through a 100 mm cell strainer and transferred to cooled PBS to remove remaining enzyme and EDTA. The cells were loaded at 40% and 75% on Percoll™ (GE Healthcare) gradients. Lymphocytes were harvested from the surface of the Percoll gradient membrane and washed with DMEM medium supplemented with 1% FBS and 1% penicillin/streptomycin. For analysis of cytokines, the cells were stimulated at 37° C. in a complete RPMI medium containing 10% FBS, 1% penicillin/streptomycin, 2 mM L-glutamine, 1 mM sodium pyruvate, non-essential amino acids and 0.1% beta-ME (v/v) with PMA (Calbiochem) and ionomycin (Calbiochem) in the presence of GolgiStop (BD Biosciences) for 4 to 5 hours. The cells were stained according to the manufacturer's protocol for flow cytometric analysis.

The following reagents were used to stain the cells:

Live/Dead fixable dye (Life Technologies), fixation/permeation buffer (eBioscience), permeation buffer (eBioscience), IC fixation buffer (eBioscience) and antibodies.

The following antibody clones were used in this experiment:

CD4 (RM4-5), CD44 (IM7), CD62L (MEL-14), CD45.1 (A20), CD103 (2E7), Foxp3 (FJK-16s), CTLA4 (UC10-4B9), Nrp1 (3E12), IL-10 (JES5-16E3), IFN-γ (XMG1.2), IL-17A (17B7), CD11c (N418), CD11b (M1/70), F4/80 (BM8), MHCII (M5/114.15.2).

4. In-Vitro Differentiation of Antigen-Presenting-Cell-Dependent T Cell $2 \times 10^4$ CD11c+ DCs derived from indicated tissues were treated with indicated polysaccharides or MGCP and incubated in RPMI 1640 complete medium for 14 hours in the presence of 10 ng/mL of GM-CSF (PeproTech). In the case of stimulating DC by treatment with MGCP, DC was stimulated with 50 μg/mL of MGCP in most in-vitro experiments, except that the MGCP concentration was indicated otherwise. The stimulated DCs were washed and co-incubated with $2 \times 10^5$ naïve CD4 T cells for 3 days. Most experiments were conducted under sub-optimal Treg cell skewing conditions comprising 0.1 μg/ml of anti-CD3 (BioXcell), 100 U/ml of IL-2, 0.1 or 0.05 ng/ml of TGF-beta1 (Miltenyi Biotech) and 10 ng/ml of GM-CSF. For the suboptimal Th1 operation environment, cells were incubated in the presence of 0.1 μg/mL of anti-CD3, 100 U/ml of IL-2, 2.5 ng/ml of IL-12, 10 ng/ml of GM-CSF and 10 μg/ml of anti-IL-4. After incubation for 3 days, the cells were analyzed by the flow cytometry described above. In some experiments, splenic DCs were treated with antagonists before stimulation with MGCP. In the case of an experimental procedure using a polysaccharide lyase, prior to treatment of spleen DC, zymosan or MGCP was digested with the same enzyme according to the manufacturer's protocol and incubated with naïve CD4 T cells. In the experiment using celecoxib, treatment with an inhibitor was performed for 30 minutes before stimulating spleen DC with MGCP, followed by incubation in combination with naïve CD4 T cells in the presence of celecoxib.

The following reagents were used in the experiment:

α-(1-6) core mannosidase (QAbio), pustulanase (Prokazyme), zymolyase (MP Biomedicals), Mincle monoclonal antibody (anti-Mincle mAb, MBL), DC-SIGN antibody (anti-DC-SIGN Ab, Abcam), recombinant mouse MMR protein (R&D systems)

5. Induction of Experimental Colitis through CD4 T Cell Delivery

Experimental colitis was induced according to previously described methods (Powrie F., Leach M. W., Mauze S., et al. Immunity 1994;1(7):553-62. and Leach M. W., Bean A. G., Mauze S., et al. Am. J. Pathol. 1996;148(5):1503-15.). Specifically, CD4+Foxp3$^{GFP}$-CD44$^{lo}$CD62L$^{hi}$ naïve T cell ($1 \times 10^6$) FACs sorted from congenic (CD45.1+) Foxp3-EGFP mice or CBir mice were delivered to Rag1-deficient mice. In order to evaluate the efficacy of Treg cells induced by MGCP generated in vitro, naïve CD4 T cells were adoptively transferred simultaneously with marked Treg cells ($2 \times 10^5$). In order to induce colitis with naive CD4 T cells from CBir mice, the recipient was orally administered with mock or MGCP every other day for the entire experimental period. The progress of colitis was monitored by measuring body weight twice a week, and mice were sacrificed after the body weight thereof had decreased to about 20%. Disease severity was analyzed by measuring the length of the colon, histological evaluation, and production of cytokines from donor naive CD4 T cells.

6. In-Vivo Adoptive Delivery

Prior to delivery of naive CD4 T cells, 200 μg of MGCP was orally administered to C57BL/6 or Dectin1−/− mice daily for 2 weeks. CD4+Foxp3$^{EGFP}$-CD44$^{lo}$CD62L$^{hi}$ naïve T cells (purified>99%, $1.5-2 \times 10^6$) isolated from Foxp3-EGFP or OT-II mice having congenic alleles were transferred to MGCP-administered deficient mice by intravenous administration, and MGCP was additionally administered thereto daily for one week. Mice receiving OT-II naive CD4 T cells were supplemented with 20 mg of OVA protein every other day for 1 week from the day before cell delivery to the end of the experiment.

7. RNA Sequencing

Mock and MGCP were administered to GF mice daily for 2 weeks. Colon CD11c+ DC derived from GF mice supplemented with mock and MGCP was isolated from whole cells of the colonic lamina propria according to the manufacturer's protocol using microbeads. Total RNA was purified from colon DCs of mice fed mock or MGCP. Ribospin TMII (GeneAll biotechnology) was used to isolate total RNA. A TruSeq stranded mRNA sample preparation kit (Illumina, San Diego, CA) was used for library preparation. RNA sequencing was performed using the NextSeq 500 sequencing platform. RNA sequence data was deposited in the Gene Expression Omnibus (NCBI) data repository (registration number GEO: RNA-seq data: GSE126937).

8. Quantitative Reverse Transcription Polymerase PCR (QrtPCR)

Whole transcripts were purified from colon CD11c+ DC derived from mock and MGCP-supplemented GF mice. The cells were harvested and then lysed in TRIzol reagent. Total RNA was purified according to the manufacturer's protocol. Purified total RNA was synthesized into cDNA using M-MLV reverse transcriptase (Promega). The expression level of the indicated marker was analyzed using the primer pairs shown in the following table and cDNA prepared by the method described above. All data were normalized to the expression level of hypoxanthine-guanine phosphoribosyl transferase (HPRT). The results were further analyzed as the expression level relative to the expression level of the mock and control groups.

Zymosan-treated DC promoted the induction of Treg cells in a concentration-dependent manner, and zymosan exhibited the highest induction performance at 500 µg/mL (FIG. 1A). Next, whether or not zymosan induces effector T cells in a similar concentration-dependent manner was determined. Zymosan induced the expression of RORγt at the lowest concentration, but did not affect the expression of T-bet (FIG. 2A). Surprisingly, the expression of T-bet and RORγt in effector T cells was inhibited in proportion to the concentration of zymosan (FIG. 2A).

In addition, in order to clearly identify the polysaccharide derived from zymosan involved in the induction of Treg cells, polysaccharides with different structures were cleaved using a cleavage enzyme. The removal of beta-1,3-glucan in zymosan dramatically increases the induction of Treg cells (FIG. 1B). Meanwhile, cleavage of beta-1,6-glucan and mannan of zymosan inhibits the induction of Treg cells and thereby exhibits the opposite effect (FIG. 1C). Cleavage of beta-1,3-glucan and beta-1,6-glucan caused an increase in the expression of RORγt compared to the non-treated control group, unrelated to the compensation of the zymosan-mediated RORγt inhibition (FIGS. 2B and 2C). The above results indicate the immunological effect of the specific polysaccharide structure of zymosan. The above results

TABLE 1

Primer nucleotide sequence

| Indicated marker | | Primer nucleotide sequence | SEQ ID NO: |
|---|---|---|---|
| HPRT | Forward | 5'-TTA TGG ACA GGA CTG AAA GAC-3' | 1 |
| | Reverse | 5'-GCT TTA ATG TAA TCC AGC AGG T-3' | 2 |
| IL-10 | Forward | 5'-ATA ACT GCA CCC ACT TCC CA-3' | 3 |
| | Reverse | 5'-TCA TTT CCG ATA AGG CTT GG-3' | 4 |
| TGF- | Forward | 5'-CTC CCG TGG CTT CTA GTG C-3' | 5 |
| | Reverse | 5'-GCC TTA GTT TGG ACA GGA TCT G-3' | 6 |
| PD-L1 | Forward | 5'-GCT CCA AAG GAC TTG TAC GTG-3' | 7 |
| | Reverse | 5'-TGA TCT GAA GGG CAG CAT TTC-3' | 8 |
| IDO | Forward | 5'-GCT TTG CTC TAC CAC ATC CAC-3' | 9 |
| | Reverse | 5'-CAG GCG CTG TAA CCT GTG T-3' | 10 |
| COX2 | Forward | 5'-TGG CTG CAG AAT TGA AAG CCC T-3' | 11 |
| | Reverse | 5'-AAA GGT GCT CGG CTT CCA GTA T-3' | 12 |

9. Histological Analysis

The clinical score of experimental colitis was measured by histological analysis through H&E staining. Briefly, 1 cm of colon was fixed in 10% formaldehyde and embedded in a paraffin segment. The paraffin segment was cut to a thickness of 3 µm and stained with Hematoxylin (Sigma-Aldrich) and Eosin (Sigma-Aldrich).

10. Statistical Analysis

Statistical analysis was performed using GraphPad Prism software (La Jolla, USA). The difference between the control group and the experimental group was evaluated using a two-tailed, unpaired Student's t-test. Data are presented as mean±SEM.

Example 1: Confirmation of Ability of Zymosan to Induce Treg Cells

In order to study the immunomodulatory function of yeast polysaccharides in the immune system, zymosan was treated with DC and then incubated with naïve CD4 T cells.

show that beta-1,6-glucan and mannan are essential for the generation of Treg cells, while beta-1,3-glucan induces a Th1 immune response and inhibits the production of Treg cells.

Example 2: Purification of MGCP and Structural and Functional Characterization Thereof The polysaccharide was purified from the yeast cell wall in the same manner as described above in Materials and Methods, and the structural properties and immune functional relevance were confirmed. The results of composition analysis showed that yeast-derived polysaccharides consist of mannose (80.6%), glucose (14.9%) and galactose (4.5%) (FIGS. 3A and 4). Further analysis of the polysaccharide structure and morphology through proton nuclear magnetic resonance (NMR) spectroscopy supported the notion that the polysaccharide contains mannan and beta-1,6-glucan as main ingredients (FIG. 5A). The detailed structure of the mannan unit was found to have an alpha-1,6-linked mannose backbone and a single-unit mannose (30%), two-unit mannose (16.8%), or three-unit mannose (28.4%) joined with alpha-1,2-linkage or alpha-1,3-linkage as a side chain (mannose without side chain (24.8%)) (FIG. 5B). The structure of the mannan component was similar to the typical mannan structure found in the cell wall of S. cerevisiae. Beta-1,6-glucan contains a beta-1,6-linked glucose backbone as a main ingredient, and 18% of the backbone glucose has a beta-1,3-linked single unit glucose as a side chain (FIG. 5C). Yeast-derived polysaccharides having such a structure are novel, and the purified polysaccharides were named "Mannan/β-Glucan Containing Polysaccharides (MGCP)".

In order to detect the molecular weight of MGCP, it was analyzed through a method known in the art using HPLC. A TSK G-G5000PWXL size exclusion column was used and 50 mM ammonium bicarbonate was flushed as an eluent at a flow rate of 0.8 ml/min. The results of analysis were detected using a differential refractive index detector and a UV detector at a wavelength of 206 nm. The reference material used to determine the molecular weight was the Dextran standard, and information thereon is shown in Table 2 below.

TABLE 2

| Dextrans (kDa) | logPM | Retention time (min) | Retention volume (mL) |
| --- | --- | --- | --- |
| 1 | 3 | 13.156 | 10.5248 |
| 5 | 3.698970004 | 12.528 | 10.0224 |
| 50 | 4.698970004 | 10.71 | 8.5680 |
| 150 | 5.176091259 | 9.843 | 7.8744 |
| 410 | 5.612783857 | 9.122 | 7.2976 |
| 670 | 5.826074803 | 8.809 | 7.0472 |

As a result of HPLC, two broad peaks were identified, and the molecular weight of MGCP was found to be 4 kDa to 60 kDa (FIG. 6 and Table 3 below). Based on the results of HPLC analysis of the entire MGCP, as shown in FIG. 6, the total MGCP was fractionated into three fractions A, B and C, and the molecular weight of each fraction was determined through HPLC (FIG. 7 and Table 3 below).

TABLE 3

| Sample | Retention time (min) | Molecular weight (kDa) |
| --- | --- | --- |
| Total MGCP | 10.529 | 59.026 |
|  | 12.020 | 7 |
|  | 12.399 | 4 |
| MGCP fraction A | 10.512 | 60 |
| MGCP fraction B | 10.593 | 53 |
|  | 11.855 | 8.9 |
| MGCP fraction C | 10.620 | 51 |
|  | 12.001 | 7 |
|  | 12.523 | 3.5 |

The immune functional relationship of MGCP was analyzed, and specifically, the ability thereof to induce Treg cells was determined. Splenic DC treated with MGCP induced Treg cells in a dose-dependent manner (FIG. 5D). In order to analyze the Treg cell induction relevance of each structure of MGCP, first, commonly available mannan, beta-1,6-glucan (Pustulan) or beta-1,3-glucan (curdlan) was independently treated. As a result, none of them was found to be able to independently induce Treg cells (FIGS. 3B and 3C). Meanwhile, as previously reported, it was found that D-(+) mannose can induce Treg cells (FIG. 3D). In order to determine the essential site of GMCP responsible for the induction of Treg cell differentiation, experiments were conducted on each structure of mannan, beta-1,6-glucan, and beta-1,3-glucan, cleaved with an enzyme that cleaves the same. Cleavage of beta-1,6-glucan in MGCP remarkably reduced the production of Treg cells, and cleavage of mannan exhibited reduced differentiation of Treg cells, but this was not a significant value (FIG. 5E). In addition, the simultaneous removal of both polysaccharides showed results similar to the case of cleaving β-1,6-glucan alone with regard to the induction of Treg cells, which means that the induction of Treg cells is mainly dependent on β-1,6-glucan (FIG. 5E). Interestingly, polysaccharides purified from β-1,3-glucan-removed yeast cell walls induced the production of more Treg cells than MGCP purified from intact yeast cell walls (FIG. 3E). These results suggest that all components of MGCP are essential factors in inducing Treg cells. The β-1,6-glucan moiety comprising a β-1,3-linked single glucose as a side chain is essential for the ability of MGCP to induce Treg cells, whereas the β-1,3-glucan moiety regulates the induction of Treg cells.

Although not shown, it was found that when the molecular weight of the polysaccharide was increased, particularly when the molecular weight was 100 kDa or more, the induction activity of Treg cells was decreased.

Example 3: Confirmation of Inflammatory Colitis Alleviation Efficacy of In-Vivo MGCP-Induced Treg Cells As described above, MGCP was found to promote the differentiation of Treg cells. Here, whether or not the in-vitro differentiated Treg cells exhibited an alleviation effect in vivo in mice with colitis was determined. Treg cells with a congenic marker (CD45.1+) were generated in vitro by treating DC with MGCP, and were adoptively transferred to recipient mice at the same time as naïve CD4 T cells, and the immune regulation function of Treg cells induced by MGCP was determined. The result showed that Treg cells induced by MGCP interfere with the progression of colitis. Specifically, weight loss and shortening of colon length were significantly reduced in mice that received MGCP-Treg cells (FIGS. 8A and 6B). Regarding the clinical symptoms of colitis, metastasis of Treg cells induced by MGCP prevents destruction of the epithelial cell structure of colon tissue and inhibits the penetration of lymphocytes into the colonic lamina propria, indicated by a histopathology score (FIGS. 8C and 6D). Since IFN-γ is known to play an important role in the pathogenesis of colitis, the production of IFN-γ, which is a pathogenic cytokine, from CD4 T cells in the colonic lamina propria was evaluated. The level of IFN-γ production of donor naïve CD4 T cells was dramatically reduced in subjects that received MGCP-Treg cells compared to those who received only naive CD4 T cells (FIG. 8E). The above results show that MGCP-induced Treg cells inhibit the production of inflammatory cytokines and ameliorate inflammatory colitis.

Example 4: Induction of Production of Colon Treg Cells through Oral Administration of MGCP In vitro, MGCP promoted the induction of Treg cells that are functionally active in vivo. In order to determine whether or not MGCP can generate Treg cells in vivo, MGCP was administered orally to mice, followed by transfer of colon naive CD4 T cells (CD45.1+). Interestingly, the administration of MGCP generated significantly higher frequency of Treg cells from donor CD4 T cells in the colon than in the control group (FIG. 9A). The Treg cells express CTLA-4, which is an important indicator of inhibitory activity of Treg cells (FIG. 9B). In addition, in the small intestine, a similar increase in the frequency of Treg cells among donor cells was observed, and they also expressed CTLA-4 (FIGS. 10A and 8B). Meanwhile, the frequency of recipient-derived Treg cells and the level of CTLA-4 expression in the host Treg cells were similar to those of the control group in the colon and small intestine (FIGS. 9C, 7D, 8C, and 8D). The absolute number of colon Treg cells in the mice treated with MGCP increased in the colon, but this increase was not a significant value (FIGS. 9E and 8E). It was observed that among the receptor Treg cells in the entire intestine of MGCP-administered mice, the number of cells expressing Helios increased (FIGS. 9F and 8F). Functionally, administration of MGCP significantly increased IL-10 production of Treg cells in the colonic lamina propria only, but did not increase the same in the small intestine (FIGS. 9G and 8G). The production of IFN-γ by effector T cells in the colonic lamina propria was reduced after MGCP treatment, but the level of IL-17A did not change (FIG. 9H). In contrast to this, the expression of IFN-γ and IL-17A in CD4 T cells of the small intestine was similar in both mock and MGCP-treated mice (FIG. 10H). Administration of MGCP induces differentiation of Treg cells from donor CD4 T cells in the intestine, but treatment with MGCP could not induce differentiation of Treg cells from host- or donor-derived CD4 T cells in the spleen or mLN (FIGS. 10I and 8J). Overall, in vivo, MGCP not only reduced IFN-γ, which is an inflammatory cytokine in colon effector CD4 T cells, but also promoted the generation of new functional colon Treg cells with enhanced IL-10 production. The above results mean that MGCP can affect the colon immunomodulatory environment under conditions of homeostasis.

Example 5: Amelioration of Colitis of Microbiota-Specific Treg Cells Induced by MGCP In order to determine whether or not MGCP induces microbial antigen-specific Treg cells and regulates inflammatory immune responses in vivo, CBir mice carrying microbial flagellin-reactive CD4 T cells were used. Naive CD4 T cells from CBir mice were transferred to Rag1−/− mice, and mock (DW) or MGCP was orally administered daily. Adoptive transfer of microbe-responsive naive CD4 T cells to mice with weakened immunity has been reported to induce experimental colitis due to the excessive immune response to symbiotic microbiota (FIG. 11A). However, supplementation with MGCP showed remarkable resistance to weight loss (FIG. 11A). In addition to the effect on body weight change, shortening of the length of the colon was also prevented by administration of MGCP (FIGS. 11B and 9C). Consistent with clinical signs, MGCP-administered mice inhibited the proliferation of epithelial cells and the penetration of lymphocytes into the colon (FIG. 11D). In addition, histopathology scores were shown to be reduced compared to mock-treated mice (FIG. 11E). These results suggest that MGCP can inhibit the production of pathogenic cytokines in the pre-inflammatory environment by promoting the generation of new functional Treg cell cells (FIGS. 8 and 9).

Therefore, whether or not treatment with MGCP could inhibit the production of harmful cytokines from the symbiotic antigen-specific CD4 T cells of the recipient mice while promoting the generation of Treg cells was determined. MGCP-administered mice increased the differentiation of microbe-reactive Treg cells from donor naïve CD4 T cells compared to mock-treated mice (FIG. 11F), and expression of CD103 and CTLA-4, which are molecules important for the stability and function of Treg cells, was similar in Treg cells of MGCP-treated and mock-treated mice (FIG. 12A). Consistent with the clinical signs of colitis, the production of IFN-γ from donor CD4 T cells was substantially regulated in MGCP-administered mice compared to mock-treated mice (FIG. 11G), but IL-17A levels were found to be similar in the colonic lamina propria (FIG. 12B). Overall, the above results indicate that MGCP induces the metastasis of Treg cells and that administration of MGCP promotes the production of Treg cells responding to the symbiotic antigen and inhibits the development of inflammatory colitis and the production of IFN-γ.

Example 6: Necessity of Cox2 for Induction of MGCP-Mediated Treg Cells by Intestinal CD103$^+$CD11b$^+$DC In order to establish the mechanism by which MGCP induces Treg cells using antigen-presenting cells, the ability of DC subsets and macrophages to induce differentiation of Treg cells by MGCP stimulation was evaluated. DCs are divided depending on the expression of CD11b and CD103 in the intestine. DC subsets and macrophages of each intestine were stimulated with MGCP and then incubated with naive CD4 T cells. Intestinal CD103$^+$CD11b$^+$DC treated with MGCP induced an approximately 10-fold increase in the production of Treg cells compared to the case of mock treatment (FIG. 13A). CD103$^+$CD11b$^-$DC and macrophages did not increase the level of Treg cells after MGCP stimulation, but efficiently induced Treg cells even when not treated with MGCP (FIGS. 13A and 14). In order to establish a mechanism by which MGCP stimulates DC to allow DC to induce Treg cells and by which a DC activation function is inhibited by microbial stimulants, DW (mock) or MGCP was administered orally to germ-free mice (GF) every day for 2 weeks. For analysis of transcriptomic configuration, CD11c$^+$DC was isolated from the colon of mock- or MGCP-treated mice. Administration of MGCP enhances the expression of tolerogenic DC-related markers such as Il10, Cd274 (PD-L1 coding gene), indoleamine 2,3-dioxygenase (IDO), and Tgfβ1 (FIGS. 13B and 11C). Interestingly, DC of MGCP-treated mice increased the expression of Ptgs2 (cyclooxygenase-2 coding gene, Cox2) about 20 times compared to DC of mock (DW)-treated mice (FIGS. 13B and 11C). Since Cox2 is already known to induce Treg cells in a tumor environment, the role of Cox2 in Treg cell differentiation by MGCP was evaluated. Splenic DCs were stimulated with MGCP and incubated with naive CD4 T cells in the presence of celecoxib, which is a Cox2-selective inhibitor. The induction of Treg cells by MGCP was remarkably reduced by inhibiting Cox2 (FIGS. 13D and 11E). These results suggest that the increase in MGCP-induced Treg cells is specifically mediated by the CD103$^+$CD11b$^+$ intestinal DC subset in a Cox2-dependent manner. In addition, MGCP modified the DC transcriptome landscape into a tolerogenic DC phenotype.

Example 7: Importance of Pattern Recognition Receptor in Mechanism of Generation of Treg Cells Induced by MGCP DCs express pattern recognition receptors (PRRs) to thereby recognize microbial antigens comprising polysaccharides present in the intestine. In order to investigate the role of the polysaccharide recognition receptors in MGCP-mediated immune regulation, the differentiation of Treg cells was confirmed using DC from mice with impaired specific receptors. Dectin1-deficient splenic DC significantly reduced the production of Treg cells by MGCP, but deficiency of Dectin2 decreased the differentiation of Treg cells to a relatively small extent (FIG. 15A). In addition, DCs deficient in each of TLR2, TLR4, and TLR6 reduced Treg cell differentiation by MGCP compared to WT DC, with TLR4 exhibiting the most remarkable effect (FIG. 15A). Consistent with the decrease in Treg cell production due to TLR deficiency in DC, DCs with impaired MyD88 signaling showed a remarkable decrease in Treg cell differentiation (FIG. 15B). In addition, antagonistic blocking antibodies of each of DC-SIGN, Mincle and mannose receptors were used to study the possible roles of different C-type lectin receptors. Blocking of the DC-SIGN signal in DC showed a partial decrease in Treg cell differentiation by MGCP, but no significant effect was observed for other receptors (FIG. 15C). Overall, the above results suggest that Dectin1 and TLR4 play an important role in the induction of Treg cells by MGCP and that MGCP induces Treg cells through various innate receptors.

Example 8: Confirmation of Importance of Dectin1 for Treg Cell Induction by MGCP In order to determine the role of Dectin1 in the generation of Treg cells induced by MGCP, mLN DCs of Dectin1-rich or Dectin1-deficient mice were stimulated with mock or MGCP. Dectin1-rich DCs showed increased expression of Cox2 and other regulatory markers after MGCP stimulation, but MGCP did not promote the expression of Cox2 in Dectin1-deficient DCs (FIGS. 16A and 15A). Consistent with the role of Dectin1 on the expression of Cox2 after MGCP treatment, Ido and Tgfβ1 transcripts were specifically increased by MGCP stimulation in Dectin1-rich DCs, but were not specifically increased in impaired DCs (FIG. 17A). Surprisingly, the absence of Dectin1 did not result in a change in the increase in MGCP-mediated expression of other regulatory DC markers such as Il10 and Cd274 (FIG. 17A). To support the essential role of Dectin1 in MGCP-induced Treg cell generation, the effect of MGCP in Dectin1-deficient mice was tested. MGCP was administered to mice that received naive CD4 T cells from OT-II mice and supplemented with ovalbumin every other day. MGCP was administered to the recipient mice throughout the experiment. Interestingly, administration of MGCP dramatically increased the differentiation of ovalbumin-activated Treg cells in the small intestine of Dectin1-rich receptors, while the effect of MGCP inducing Treg cell differentiation was reduced in Dectin1-deficient mice (FIGS. 16B and 14C). Meanwhile, the frequency of Treg cells among the recipient-derived cells in the Dectin1-deficient or Dectin1-rich receptors was similar in the case of mock and MGCP treatment (FIG. 17B). The frequency of Treg cells derived from host cells of MGCP-treated Dectin1 intact mice was similar to that of mock-treated mice, but the number of Treg cells was significantly increased in the presence of MGCP only in Dectin1-rich mice, but not in Dectin1-deficient mice (FIG. 17C). Interestingly, MGCP administration increased the frequency of inducible Treg cells, among recipient-derived cells, in Dectin1-rich mice, but not in Dectin1-knockout mice (FIGS. 16D and 14E). In addition, whether or not MGCP affects the induction of Treg cells in the mesenteric lymph nodes of these mice was evaluated. Although the frequency of Treg cell differentiation increased in Dectin1 intact mice, the effect of MGCP could be neglected in Dectin1 knockout mice (FIG. 17D). Overall, these findings suggest that the molecular mechanism of in-vivo Treg cell induction by MGCP is dependent on Dectin1, which is mediated by Cox2 upregulation of DC.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The novel polysaccharide according to the present invention generates tolerogenic antigen-presenting cells through beta-glucan and mannan structures of the polysaccharide even at low doses, and induces the differentiation or production of antigen-specific regulatory T cells (Treg cells) to thereby regulate the target immune system with few side effects. Therefore, MGCP and Treg cells induced by the polysaccharide are useful for the prevention and treatment of immune diseases and inflammatory diseases.

The invention claimed is:

1. A method of immunomodulation, comprising administering a pharmaceutical composition or a food composition containing a polysaccharide,
   wherein the polysaccharide comprises beta-glucan (β-glucan) as an active ingredient to a subject in need thereof,
   wherein the beta-glucan (β-glucan) comprises
   (i) a β-1,6-linked glucose backbone; and
   (ii) a β-1,3-linked glucose side chain,
   wherein the immunomoduation is immune suppression.

2. The method of claim 1, wherein the polysaccharide further comprises mannan having an alpha-1,6-linked (α-1,6-linked) mannose backbone.

3. The method of claim 2, wherein the mannan comprises:
   i) an α-1,6-linked mannose backbone; and
   ii) at least one side chain selected from the group consisting of α-1,2-linked or α-1,3-linked single-unit mannose, α-1,2-linked or α-1,3-linked two-unit mannose and α-1,2-linked or α-1,3-linked three-unit mannose.

4. The method of claim 3, wherein the polysaccharide comprises the single-unit mannose side chain, the two-unit mannose side chain, the three-unit mannose side chain, and the mannose backbone having no side chain at a content ratio of 20% to 40%: 10% to 30%: 20% to 40%: 20% to 40%.

5. The method of claim 1, wherein the polysaccharide has a molecular weight of 4 kDa to 60 kDa.

6. The method of claim 1, wherein the β-glucan comprises:
   (i) a β-1,6-linked glucose backbone; and
   (ii) a β-1,3-linked single-unit glucose side chain.

7. The method of claim 6, wherein the β-1,3-linked single-unit glucose side chain is comprised in a proportion of 10% to 30% with respect to the total glucose.

8. The method of claim 1, wherein the polysaccharide further comprises mannan.

9. The method of claim 1, wherein the polysaccharide induces regulatory T cells (Treg cells).

10. The method of claim 9, wherein the regulatory T cells (Treg cells) are CD4+Foxp3+ regulatory T cells.

11. The method of claim 1, wherein the polysaccharide is derived from yeast.

12. The method of claim 8, wherein the polysaccharide comprises the mannose and the glucose at a content ratio of 70% to 90%: 10% to 30%.

\* \* \* \* \*

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: HPRT primer Forward

<400> SEQUENCE: 1
ttatggacag gactgaaaga c                    21

<210> SEQ ID NO 2
<211> LENGTH: 22
<212> TYPE: DNA
<213> ORGANISM: Artificial Sequence
<220> FEATURE:
<223> OTHER INFORMATION: HPRT primer Reverse

```
<400> SEQUENCE: 2
gctttaatgt aatccagcag gt                                        22

<210> SEQ ID NO 3
<211> LENGTH: 20
<212> TYPE: DNA
<213> ORGANISM: Artificial Sequence
<220> FEATURE:
<223> OTHER INFORMATION: IL-10 primer Forward

<400> SEQUENCE: 3
ataactgcac ccacttccca                                           20

<210> SEQ ID NO 4
<211> LENGTH: 20
<212> TYPE: DNA
<213> ORGANISM: Artificial Sequence
<220> FEATURE:
<223> OTHER INFORMATION: IL-10 primer Reverse

<400> SEQUENCE: 4
tcatttccga taaggcttgg                                           20

<210> SEQ ID NO 5
<211> LENGTH: 19
<212> TYPE: DNA
<213> ORGANISM: Artificial Sequence
<220> FEATURE:
<223> OTHER INFORMATION: TGF-beta primer Forward

<400> SEQUENCE: 5
ctcccgtggc ttctagtgc                                            19

<210> SEQ ID NO 6
<211> LENGTH: 22
<212> TYPE: DNA
<213> ORGANISM: Artificial Sequence
<220> FEATURE:
<223> OTHER INFORMATION: TGF-beta primer Reverse

<400> SEQUENCE: 6
gccttagttt ggacaggatc tg                                        22

<210> SEQ ID NO 7
<211> LENGTH: 21
<212> TYPE: DNA
<213> ORGANISM: Artificial Sequence
<220> FEATURE:
<223> OTHER INFORMATION: PD-L1 primer Forward

<400> SEQUENCE: 7
gctccaaagg acttgtacgt g                                         21

<210> SEQ ID NO 8
<211> LENGTH: 21
<212> TYPE: DNA
<213> ORGANISM: Artificial Sequence
<220> FEATURE:
<223> OTHER INFORMATION: PD-L1 primer Reverse

<400> SEQUENCE: 8
tgatctgaag ggcagcattt c                                         21

<210> SEQ ID NO 9
<211> LENGTH: 21
```

```
<212> TYPE: DNA
<213> ORGANISM: Artificial Sequence
<220> FEATURE:
<223> OTHER INFORMATION: IDO primer Forward

<400> SEQUENCE: 9
gctttgctct accacatcca c                                              21

<210> SEQ ID NO 10
<211> LENGTH: 19
<212> TYPE: DNA
<213> ORGANISM: Artificial Sequence
<220> FEATURE:
<223> OTHER INFORMATION: IDO primer Reverse

<400> SEQUENCE: 10
caggcgctgt aacctgtgt                                                 19

<210> SEQ ID NO 11
<211> LENGTH: 22
<212> TYPE: DNA
<213> ORGANISM: Artificial Sequence
<220> FEATURE:
<223> OTHER INFORMATION: COX2 primer Forward

<400> SEQUENCE: 11
tggctgcaga attgaaagcc ct                                             22

<210> SEQ ID NO 12
<211> LENGTH: 22
<212> TYPE: DNA
<213> ORGANISM: Artificial Sequence
<220> FEATURE:
<223> OTHER INFORMATION: COX2 primer Reverse

<400> SEQUENCE: 12
aaaggtgctc ggcttccagt at                                             22
```